US008143010B2

(12) United States Patent
Lin

(10) Patent No.: US 8,143,010 B2
(45) Date of Patent: Mar. 27, 2012

(54) PROSTATE-SPECIFIC POLYPEPTIDE PAMP AND ENCODING NUCLEIC ACID MOLECULES

(75) Inventor: Biaoyang Lin, Bothell, WA (US)

(73) Assignee: Institute for Systems Biology, Seattle, WA (US)

(*) Notice: Subject to any disclaimer, the term of this patent is extended or adjusted under 35 U.S.C. 154(b) by 7 days.

(21) Appl. No.: 12/163,889

(22) Filed: Jun. 27, 2008

(65) Prior Publication Data

US 2009/0042202 A1    Feb. 12, 2009

Related U.S. Application Data

(63) Continuation of application No. 09/729,653, filed on Dec. 4, 2000, now Pat. No. 7,393,921.

(51) Int. Cl.
G01N 33/48     (2006.01)
G01N 33/483    (2006.01)
G01N 33/487    (2006.01)
G01N 33/49     (2006.01)
G01N 33/493    (2006.01)

(52) U.S. Cl. .......... 435/6.14; 435/6.1; 436/504; 436/63; 436/64

(58) Field of Classification Search ............ 435/6.1, 435/6.14; 436/504, 63, 64
See application file for complete search history.

(56) References Cited

U.S. PATENT DOCUMENTS

| | | | |
|---|---|---|---|
| 4,376,110 A | 3/1983 | David et al. | |
| 4,778,751 A | 10/1988 | El Shami et al. | |
| 5,264,563 A | 11/1993 | Huse | |
| 5,580,859 A | 12/1996 | Felgner et al. | |
| 5,679,647 A | 10/1997 | Carson et al. | |
| 5,703,055 A | 12/1997 | Felgner | |
| 5,861,248 A | 1/1999 | Russell et al. | |
| 6,383,787 B1 * | 5/2002 | Schupp et al. | 435/183 |
| 6,733,992 B2 * | 5/2004 | Ye et al. | 435/69.1 |
| 7,439,326 B2 * | 10/2008 | St. George-Hyslop et al. | 530/350 |
| 7,862,815 B2 * | 1/2011 | Cuttitta et al. | 424/139.1 |

FOREIGN PATENT DOCUMENTS

WO    WO 00/65067    11/2000

OTHER PUBLICATIONS

Itoh et al, 1998, Endocrinology, 139:1378-1388.*
Tian, Jet al, 2004 (Physiol Genomics, 17: 170-182).*
Stedman's medical dictionary, 25th ed, 1990, p. 1029-1030.*
Jansen, M et al, 1995, Pediatric Res, 37 (6): 681-686.
Alberts et al. Molecular Biology of the Cell, 3rd edition, 1994, p. 465.
Shantz and Peg. Int J of Biochem and Cell Biol., 1999, vol. 31, pp. 107-122.
McClean and Hill. Eur J of Cancer, 1993, vol. 29A, pp. 2243-2248.
Fu et al, EMBO Journal, 1996, vol. 15, pp. 4392-4401.
Yokota, J et al (Oncogene, 1988,vol. 3, pp. 471-475.

Gelmini S et al, 2001, Clin Chem Lab Med, 39(5): 385-91.
Kibel, AS et al, 2000, J urol, 164(1): 192-6.
Ren, C et al, 1998, Cancer Res, 58(6): 1285-90.
Gingrich, JR et al, 1996, Cancer res, 56(18): 4096-4102.
Burgess et al. Journal of Cell Biology, 1990, 11: 2129-2138.
Lazar et al. Molecular and Cell Biology, 1988, 1247-1252.
Tao. et al. The Journal of Immunology, 1989, 143(8): 2595-2601.
Gillies et al. Human Antibodies and Hybridomas, 1990, 1(1): 47-54.
Nagase T et al, 2000, Genbank Sequence Database (Accession No. Q9HCD4 ) and MPSRCH search report, 2002, us-09-729653-2.rspt, pp. 1-2.
Kawakami T et al, 2000, GenBank Sequence Database (Accession No. Q9H5S0) and MPSRCH search report, 2002, us-09-729653-2.rspt, p. 3.
Steward, C A, 1998, Genbank Sequence Database (Accession No. 046018), and MPSRCH search report, 2002, us-09-729653-2.rspt, p. 4.
Drexler et al. Leukemia and Lymphoma,1993, 9:1-25.
Embleton et al. Immunol Ser, 1984, 23:181-207.
Hsu : In Tissue Culture Methods and Applications, Kruse and Patterson, Eds, 1973, Academic Press, NY, see abstract, p. 764.
Freshney. Culture of Animal Cells, A Manual of Basic Technique, Alan R. Liss, Inc., 1983, New York, p. 4.
Dermer (Bio/Technology, 1994, 12:320.
Schmid S et al, 2001, J comparative Neurology, 430(2): 160-71.
Conner et al, 1996, Mol Brain Res, 42: 1-17.
Bowie (Science, 1990, 257:1306-1310).
GenBank Accession No. AA363808: EST4273 Pancreas II *Homo sapiens* cDNA 5' end, mRNA sequence, prt. Feb. 15, 2001.
GenBank Accession No. AAF57545: CG11237 Gene product [*Drosophila melanogaster*], prt . Feb. 15, 2001.
GenBank Accession No. AB046858: *Homo sapiens* mRNA for KIAA1638 protein, partial cds, prt. Feb. 15, 2001.
GenBank Accession No. AK026780: *Homo sapiens* cDNA: FLJ23127 fis, clone LNG08350, prt. Feb. 15, 2001.
GenBank Accession No. AW959484: EST371554 MAGE resequences, MAGF *Homo sapiens* cDNA, mRNA sequence, prt. Feb. 15, 2001.
GenBank Accession No. BE165930: MR3-HTO487-290100-103-f03 HT0487 *Homo sapiens* cDNA, mRNA sequence, prt. Feb. 15, 2001.
GenBank Accession No. BE893201: 601436910F1 NIH.sub.—MGC.sub.—72 *Homo sapiens* cDNA clone Image:3921746 5', mRNA sequence, prt. Feb. 15, 2001.
GenBank Accession No. T27880: Hypothetical protein ZK520.1—*Caenorhabditis elegans*, prt. Feb. 27, 2001.
GenBank Accession No. CAB07299: ZK520.1 [*Caenorhabditis elegans*], prt. Feb. 27, 2001.
GenBank Accession No. CAB07301: ZK520.3 [*Caenorhabditis elegans*], prt. Feb. 27, 2001.
GenBank Accession No. Z92822: *Caenorhabditis elegans* cosmid ZK520, complete sequence, prt. Feb. 26, 2001.
Deguchi et al., "Micrometastasis of prostate cancer to lymph nodes: detection by means of reverse transcription-polymerase chain reaction," J. Natl. Cancer Inst. 89:1471-1473 (1997).

(Continued)

*Primary Examiner* — Alana Harris Dent
*Assistant Examiner* — Anne Holleran
(74) *Attorney, Agent, or Firm* — Morrison & Foerster LLP

(57) ABSTRACT

The present invention relates to novel prostate specific nucleic acid molecules and polypeptides and related methods for diagnosing or predicting susceptibility to a prostate neoplastic condition.

10 Claims, 13 Drawing Sheets

OTHER PUBLICATIONS

Ficazzola and Taneja, "Prospects for gene therapy in human prostate cancer," Mol. Med. Today 4:494-504 (1998).
Kahn et al., "Radioimmunoscintigraphy with .sup.111indium labeled CYT-356 for the detection of occult prostate cancer recurrence," Journal of Urology 152:1490-1495 (1994).
Narod, "Genetic epidemiology of prostate cancer," Biochim. Biophys. Acta. 1423:F1-13 (1999).
Neal et al., "Unanswered questions in screening for prostate cancer," Eur. J. Cancer 36:1316-1321 (2000).
Nupponen and Visakorpi, "Molecular biology of progression of prostate cancer," Eur. Urol. 35:351-354 (1999).
Small, "Advances in prostate cancer," Curr. Opin. Oncol. 11:226-235 (1999).
Ablin, "A retrospective and prospective overview of prostate-specific antigen," J. Cancer Res. Clin. Oncol. 123:583-594 (1997).
Blok et al., "Isolation or cDNAs that are differently expressed between androgen-dependent and androgen-independent prostate carcinoma cells using differential display PCR," The Prostate 26:213-224 (1995).
Bussemakers et al., "DD3: A New prostate-specific gene, highly overexpressed in prostate cancer," Cancer Research 59:5975-5979 (1999).
Nelson et al., "An expressed-sequence-tag database of the human prostate: sequence analysis of 1168 cDNA clones," Genomics 47:12-25 (1998).
Srikantan et al., "PCGEM1, a prostate-specific gene, is overexpressed in prostate cancer," Proc. Natl. Acad. Sci. USA 97:12216-12221 (2000).
Vasmatzis et al., "Discovery of three genes specifically expressed in human protstate by expressed sequence tag database analysis," Proc. Natl. Acad. Sci. USA 95:300-304 (1998).
GenBank Accession No. AW629941, Mar. 6, 2000.
Altschul et al., Nucleic Acids Res., 25:3389-3402 (1997).
Ausubel et al., Current Protocols in Molecular Biology (Supplement 47), John Wiley & Sons, New York (1999).
Borrabeck, Antibody Engineering, 2D ED., Oxford University (1995).
Campbell's Urology, Seventh Edition, W.B. Saunders Company, Philadelphia (1998).
Dieffenback, C.W. et al., PCR Printer: A Laboratory Manual, Cold Spring Harbor Press, Plainview, New York (1995).
Donnelly et al., Ann. Rev. Immunol., 15:617-648 (1997).
Eichler et al., Med. Res. Rev., 15:481-496 (1995).
Eichmann et a., CRC Critical Reviews in Immunology, 7:193-227 (1987).
Francis et al., Curr. Opin. Chem. Biol., 2:422-428 (1998).
Gordon et al., Acc. Chem. Res., 29:144-154 (1996).
Gordon et al., J. Med. Chem., 37:1233-1251 (1994).
Gordon et al., J. Med. Chem., 37:1385-1401 (1994).
Harlow and Lane, Antibodies: A Laboratory Manual, Cold Spring Harbor Laboratory Press (1988).
Hilyard et. al., Protein Engineering: A practical approach IRL Press (1992).
Huse et al., Science, 246:1275-1281 (1989).
Sambrook et al., Molecular Cloning: A Laboratory Manual, 2nd ed., Cold Spring Harbor Press, Plainview, New York (1989).
Sofia, Mol. Divers, 3:75-94 (1998).
Tatiana et al., FEMS Microbiol Lett., 174:247-250 (1999).
Thompson et al., Nucleic Acids Res., 22:4673-4680 (1994).
Tietze al., Curr. Biol., 2:363-371 (1998).
Ward et al., Nature, 341:544-546 (1989).
Wilson et al., Combinational Chemistry: Synthesis and Application, John Wiley & Sons, New York (1997).
Winter and Harris, Immunol. Today, 14:243-246 (1993).

* cited by examiner

Sequence Range: 1 to 4500

```
              10         20         30         40         50         60
      CACTCGCTGATTGGTCGCTGCTCGCGCGGTCTCCTGGGTGACGGGAACGCGGTAGCCTGC
      GTGAGCGACTAACCAGCGACGAGCGCGCCAGAGGACCCACTGCCCTTGCGCCATCGGACG
       H   S   L   I   G   R   C   S   R   G   L   L   G   D   N   A   V   A   C>

70         80         90        100        110        120
      TTGGTGGAGACCGGGTGCGCCTGCGTACTTCATAGTTCGCGTAGCGGCTCGAGCGTGGAG
      AACCACCTCTGGCCCACGCGGACGCATGAAGTATCAAGCGCATCGCCGAGCTCGCACCTC
       L   V   E   T   G   C   A   C   V   L   H   S   S   R   S   G   S   S   V   E>

130        140        150        160        170        180
      ATGAAGCGTATTTTCTCACTGCTAGAAAAGACTTGGCTTGGCGCACCAATACAGTTTGCC
      TACTTCGCATAAAAGAGTGACGATCTTTTCTGAACCGAACCGCGTGGTTATGTCAAACGG
       M   K   R   I   F   S   L   L   E   K   T   W   L   G   A   P   I   Q   F   A>

190        200        210        220        230        240
      TGGCAAAAAACATCAGGAAACTACCTTGCAGTAACAGGAGCTGATTATATTGTGAAAATC
      ACCGTTTTTTGTAGTCCTTTGATGGAACGTCATTGTCCTCGACTAATATAACACTTTTAG
       W   Q   K   T   S   G   N   Y   L   A   V   T   G   A   D   Y   I   V   K   I>

250        260        270        280        290        300
      TTTGATCGCCATGGTCAAAAAAGAAGTGAAATTAACTTACCTGGTAACTGTGTTGCCATG
      AAACTAGCGGTACCAGTTTTTTCTTCACTTTAATTGAATGGACCATTGACACAACGGTAC
       F   D   R   H   G   Q   K   R   S   E   I   N   L   P   G   N   C   V   A   M>

310        320        330        340        350        360
      GATTGGGATAAAGATGGAGATGTCCTAGCAGTGATTGCTGAGAAATCTAGCTGCATTTAT
      CTAACCCTATTTCTACCTCTACAGGATCGTCACTAACGACTCTTTAGATCGACGTAAATA
       D   W   D   K   D   G   D   V   L   A   V   I   A   E   K   S   S   C   I   Y>

370        380        390        400        410        420
      CTTTGGGATGCCAACACAAATAAGACCAGCCAGTTAGACAATGGCATGAGGGATCAAATG
      GAAACCCTACGGTTGTGTTTATTCTGGTCGGTCAATCTGTTACCGTACTCCCTAGTTTAC
       L   W   D   A   N   T   N   K   T   S   Q   L   D   N   G   M   R   D   Q   M>

430        440        450        460        470        480
      TCTTTCCTTCTTTGGTCAAAAGTTGGAAGTTTCCTGGCTGTTGGAACTGTTAAAGGAAAT
      AGAAAGGAAGAAACCAGTTTTCAACCTTCAAAGGACCGACAACCTTGACAATTTCCTTTA
       S   F   L   L   W   S   K   V   G   S   F   L   A   V   G   T   V   K   G   N>
```

Figure 1A

```
       490        500        510        520        530        540
TTGSTTATTTATAATCATCAGACATCTCGAAAGATTCCTGTCCTTGGAAAACATACTAAG
AACSAATAAATATTAGTAGTCTGTAGAGCTTTCTAAGGACAGGAACCTTTTGTATGATTC
  L   X   I   Y   N   H   Q   T   S   R   K   I   P   V   L   G   K   H   T   K>
       550        560        570        580        590        600
AGAATCACTTGTGGATGTTGGAATGCAGAAAATCTGCYTGCTTTAGGTGGTGAAGATAAA
TCTTAGTGAACACCTACAACCTTACGTCTTTTAGACGRACGAAATCCACCACTTCTATTT
  R   I   T   C   G   W   N   A   E   N   L   X   A   L   G   G   E   D   K>
       610        620        630        640        650        660
ATGATTACAGTTAGTAATCAGGAAGGTGACACGATAAGACAGACACAAGTGAGATCAGAG
TACTAATGTCAATCATTAGTCCTTCCACTGTGCTATTCTGTCTGTGTTCACTCTAGTCTC
  M   I   T   V   S   N   Q   E   G   D   T   I   R   Q   T   Q   V   R   S   E>
       670        680        690        700        710        720
CCTAKCAACATGCAGTTTTTCTTGATGAAGATGGATGACCGAACCTCTGCTGCTGAAAGC
GGATMGTTGTACGTCAAAAAGAACTACTTCTACCTACTGGCTTGGAGACGACGACTTTCG
  P   X   N   M   Q   F   F   L   M   K   M   D   D   R   T   S   A   A   E   S>
       730        740        750        760        770        780
ATGATAAGTGTGGTGCTTGGCAAGAAAACTTTGTTTTTTTTTAAATCTGAATGAACCAGAT
TACTATTCACACCACGAACCGTTCTTTTGAAACAAAAAAAATTTAGACTTACTTGGTCTA
  M   I   S   V   V   L   G   K   K   T   L   F   F   L   N   L   N   E   P   D>
       790        800        810        820        830        840
AACCCAGCTGATCTTGAATTTCAGCAGGACTTTGGCAACATTGTCTGCTATAATTGGTAT
TTGGGTCGACTAGAACTTAAAGTCGTCCTGAAACCGTTGTAACAGACGATATTAACCATA
  N   P   A   D   L   E   F   Q   Q   D   F   G   N   I   V   C   Y   N   W   Y>
       850        860        870        880        890        900
GGTGATGGCCGCATCATGATTGGTTTTTTCATGTGGACATTTTGTGGTCATTTCTACTCAT
CCACTACCGGCGTAGTACTAACCAAAAAGTACACCTGTAAAACACCAGTAAAGATGAGTA
  G   D   G   R   I   M   I   G   F   S   C   G   H   F   V   V   I   S   T   H>
       910        920        930        940        950        960
ACTGGAGAGCTTGGTCAAGAGATATTTCAGGCTCGTAACCATAAAGATAATCTAACCAGC
TGACCTCTCGAACCAGTTCTCTATAAAGTCCGAGCATTGGTATTTCTATTAGATTGGTCG
  T   G   E   L   G   Q   E   I   F   Q   A   R   N   H   K   D   N   L   T   S>
```

Figure 1B

```
       970       980       990      1000      1010      1020
ATTGCAGTATCACAGACTCTTAACAAAGTTGCTACATGTGGAGATAACTGCATTAAAATC
TAACGTCATAGTGTCTGAGAATTGTTTCAACGATGTACACCTCTATTGACGTAATTTTAG
  I  A  V  S  Q  T  L  N  K  V  A  T  C  G  D  N  C  I  K  I>

1030      1040      1050      1060      1070      1080
CAAGACTTGGTTGACTTAAAAGACATGTATGTTATACTCAACCTGGATGAGGAAAATAAA
GTTCTGAACCAACTGAATTTTCTGTACATACAATATGAGTTGGACCTACTCCTTTTATTT
  Q  D  L  V  D  L  K  D  M  Y  V  I  L  N  L  D  E  E  N  K>

1090      1100      1110      1120      1130      1140
GGATTGGGTACCTTGTCCTGGACTGATGATGGCCAGTTGCTAGCACTCTCTACCCAAAGG
CCTAACCCATGGAACAGGACCTGACTACTACCGGTCAACGATCGTGAGAGATGGGTTTCC
  G  L  G  T  L  S  W  T  D  D  G  Q  L  L  A  L  S  T  Q  R>

1150      1160      1170      1180      1190      1200
GGCTCACTTCATGTTTTCCTGACCAAGCTTCCCATACTTGGGGATGCCTGCAGCACAAGG
CCGAGTGAAGTACAAAAGGACTGGTTCGAAGGGTATGAACCCCTACGGACGTCGTGTTCC
  G  S  L  H  V  F  L  T  K  L  P  I  L  G  D  A  C  S  T  R>

1210      1220      1230      1240      1250      1260
ATTGCCTATCTCACCTCCCTCCTTGAAGTCACCGTAGCCAACCCTGTTGAAGGAGAGCTA
TAACGGATAGAGTGGAGGGAGGAACTTCAGTGGCATCGGTTGGGACAACTTCCTCTCGAT
  I  A  Y  L  T  S  L  L  E  V  T  V  A  N  P  V  E  G  E  L>

1270      1280      1290      1300      1310      1320
CCAATCACAGTTTCTGTTGATGTGGAACCCAACTTTGTGGCAGTAGGTCTTTATCATCTG
GGTTAGTGTCAAAGACAACTACACCTTGGGTTGAAACACCGTCATCCAGAAATAGTAGAC
  P  I  T  V  S  V  D  V  E  P  N  F  V  A  V  G  L  Y  H  L>

1330      1340      1350      1360      1370      1380
GCTGTAGGAATGAATAATCGAGCTTGGTTTTATGTCCTTGGAGAAAATGCTGTGAAAAAA
CGACATCCTTACTTATTAGCTCGAACCAAAATACAGGAACCTCTTTTACGACACTTTTTT
  A  V  G  M  N  N  R  A  W  F  Y  V  L  G  E  N  A  V  K  K>

1390      1400      1410      1420      1430      1440
TTGAAAGATATGGAGTATCTGGGAACAGTAGCCAGTATTTGCCTTCATTCTGACTATGCT
AACTTTCTATACCTCATAGACCCTTGTCATCGGTCATAAACGGAAGTAAGACTGATACGA
  L  K  D  M  E  Y  L  G  T  V  A  S  I  C  L  H  S  D  Y  A>
```

Figure 1C

```
      1450      1460      1470      1480      1490      1500
GCTGCACTTTTTGAAGGCAAAGTCCAGTTACATTTGATAGAAAGCGAAATCTTGGATGCT
CGACGTGAAAAACTTCCGTTTCAGGTCAATGTAAACTATCTTTCGCTTTAGAACCTACGA
 A  A  L  F  E  G  K  V  Q  L  H  L  I  E  S  E  I  L  D  A>

1510      1520      1530      1540      1550      1560
CAAGAAGAACGTGAGACTCGGCTTTTCCCAGCAGTGGATGATAAGTGCCGTATCTTATGC
GTTCTTCTTGCACTCTGAGCCGAAAAGGGTCGTCACCTACTATTCACGGCATAGAATACG
 Q  E  E  R  E  T  R  L  F  P  A  V  D  D  K  C  R  I  L  C>

1570      1580      1590      1600      1610      1620
CATGCCTTAACTAGTGATTTCCTCATCTATGGTACAGATACTGGTGTCGTTCAGTATTTC
GTACGGAATTGATCACTAAAGGAGTAGATACCATGTCTATGACCACAGCAAGTCATAAAG
 H  A  L  T  S  D  F  L  I  Y  G  T  D  T  G  V  V  Q  Y  F>

1630      1640      1650      1660      1670      1680
TACATTGAAGACTGGCAATTCGTTAATGATTATCGACATCCTGTCAGTGTGAAAAAGATT
ATGTAACTTCTGACCGTTAAGCAATTACTAATAGCTGTAGGACAGTCACACTTTTTCTAA
 Y  I  E  D  W  Q  F  V  N  D  Y  R  H  P  V  S  V  K  K  I>

1690      1700      1710      1720      1730      1740
TTTCCCGACCCAAATGGGACCAGATTAGTTTTCATTGATGAAAAAAGTGATGGATTTGTT
AAAGGGCTGGGTTTACCCTGGTCTAATCAAAAGTAACTACTTTTTTCACTACCTAAACAA
 F  P  D  P  N  G  T  R  L  V  F  I  D  E  K  S  D  G  F  V>

1750      1760      1770      1780      1790      1800
TACTGTCCAGTCAATGACGCTACCTATGAGATTCCAGATTTTTTCACCAACCATTAAAGGT
ATGACAGGTCAGTTACTGCGATGGATACTCTAAGGTCTAAAAAGTGGTTGGTAATTTCCA
 Y  C  P  V  N  D  A  T  Y  E  I  P  D  F  S  P  T  I  K  G>

1810      1820      1830      1840      1850      1860
GTTCTTTGGGAAAACTGGCCAATGGATAAAGGTGTATTTATTGCTTATGATGATGATAAG
CAAGAAACCCTTTTGACCGGTTACCTATTTCCACATAAATAACGAATACTACTACTATTC
 V  L  W  E  N  W  P  M  D  K  G  V  F  I  A  Y  D  D  K>

1870      1880      1890      1900      1910      1920
GTGTACACTTATGTCTTTCACAAGGACACTATACAAGGAGCCAAGGTTATTTTGGCTGGT
CACATGTGAATACAGAAAGTGTTCCTGTGATATGTTCCTCGGTTCCAATAAAACCGACCA
 V  Y  T  Y  V  F  H  K  D  T  I  Q  G  A  K  V  I  L  A  G>
```

Figure 1D

```
          1930      1940      1950      1960      1970      1980
      AGCACCAAAGTTCCTTTTGCTCATAAACCTTTGCTGCTATATAATGGAGAGCTGACCTGC
      TCGTGGTTTCAAGGAAAACGAGTATTTGGAAACGACGATATATTACCTCTCGACTGGACG
       S  T  K  V  P  F  A  H  K  P  L  L  L  Y  N  G  E  L  T  C>

1990      2000      2010      2020      2030      2040
      CAAACACAGAGTGGAAAAGTAAACAACATCTACCTTAGCACCCATGGCTTTCTCAGCAAC
      GTTTGTGTCTCACCTTTTCATTTGTTGTAGATGGAATCGTGGGTACCGAAAGAGTCGTTG
       Q  T  Q  S  G  K  V  N  N  I  Y  L  S  T  H  G  F  L  S  N>

2050      2060      2070      2080      2090      2100
      TTAAAAGATASGGGGCCTGACGAACTGAGACCAATGCTGGCACACAATTTAATGCTAAAG
      AATTTTCTATSCCCCGGACTGCTTGACTCTGGTTACGACCGTGTGTTAAATTACGATTTC
       L  K  D  X  G  P  D  E  L  R  P  M  L  A  H  N  L  M  K>

2110      2120      2130      2140      2150      2160
      AGGTTTTCTGATGCTTGGGAAATGTGCAGGATTCTGAATGATGAGGCTGCCTGGAATGAG
      TCCAAAAGACTACGAACCCTTTACACGTCCTAAGACTTACTACTCCGACGGACCTTACTC
       R  F  S  D  A  W  E  M  C  R  I  L  N  D  E  A  A  W  N  E>

2170      2180      2190      2200      2210      2220
      TTGGCCAGAGCTTGTCTACATCACATGGAAGTGGAGTTTGCAATCCGTGTTTATCGGAGA
      AACCGGTCTCGAACAGATGTAGTGTACCTTCACCTCAAACGTTAGGCACAAATAGCCTCT
       L  A  R  A  C  L  H  H  M  E  V  E  F  A  I  R  V  Y  R  R>

2230      2240      2250      2260      2270      2280
      ATTGGAAATGTTGGCATAGTGATGTCCTTGGAACAAATAAAGGGAATAGAGGACTACAAT
      TAACCTTTACAACCGTATCACTACAGGAACCTTGTTTATTTCCCTTATCTCCTGATGTTA
       I  G  N  V  G  I  V  M  S  L  E  Q  I  K  G  I  E  D  Y  N>

2290      2300      2310      2320      2330      2340
      CTTTTTGGCAGGACACCTTGCCATGTTTACCAACGATTATAACCTGGCTCAGGACTTGTAC
      GAAAACCGTCCTGTGGAACGGTACAAATGGTTGCTAATATTGGACCGAGTCCTGAACATG
       L  L  A  G  H  L  A  M  F  T  N  D  Y  N  L  A  Q  D  L  Y>

2350      2360      2370      2380      2390      2400
      CTTGCATCCAGCTGTCCTATTGCTGCCCTGGAGATGAGAAGGGATTTACAGCATTGGGAC
      GAACGTAGGTCGACAGGATAACGACGGGACCTCTACTCTTCCCTAAATGTCGTAACCCTG
       L  A  S  S  C  P  I  A  A  L  E  M  R  R  D  L  Q  H  W  D>

2410      2420      2430      2440      2450      2460
      AGTGCTCTACAACTGGCAAAGCATTTGGCCCCAGACCAGATACCTTTTATATCAAAAGAA
      TCACGAGATGTTGACCGTTTCGTAAACCGGGGTCTGGTCTATGGAAAATATAGTTTTCTT
       S  A  L  Q  L  A  K  H  L  A  P  D  Q  I  P  F  I  S  K  E>

2470      2480      2490      2500      2510      2520
      TATGCTATTCAGCTTGAATTCGCGGGTGATTATGTAAATGCTTTGGCTCATTATGAGAAA
      ATACGATAAGTCGAACTTAAGCGCCCACTAATACATTTACGAAACCGAGTAATACTCTTT
       Y  A  I  Q  L  E  F  A  G  D  Y  V  N  A  L  A  H  Y  E  K>
```

Figure 1E

```
          2530      2540      2550      2560      2570      2580
     GGAATAACAGGTGATAATAAGGAACATGATGAAGCTTGTCTGGCTGGAGTGGCCCAGATG
     CCTTATTGTCCACTATTATTCCTTGTACTACTTCGAACAGACCGACCTCACCGGGTCTAC
      G  I  T  G  D  N  K  E  H  D  E  A  C  L  A  G  V  A  Q  M>

2590      2600      2610      2620      2630      2640
     TCCATAAGAATGGGAGACATACGTCGAGGGGTTAACCAAGCCCTCAAGCATCCCAGCAGG
     AGGTATTCTTACCCTCTGTATGCAGCTCCCCAATTGGTTCGGGAGTTCGTAGGGTCGTCC
      S  I  R  M  G  D  I  R  R  G  V  N  Q  A  L  K  H  P  S  R>

2650      2660      2670      2680      2690      2700
     GTCCTTAAAAGAGACTGTGGAGCCATATTGGAGAATATGAAGCAATTTTCAGAAGCGGCC
     CAGGAATTTTCTCTGACACCTCGGTATAACCTCTTATACTTCGTTAAAAGTCTTCGCCGG
      V  L  K  R  D  C  G  A  I  L  E  N  M  K  Q  F  S  E  A  A>

2710      2720      2730      2740      2750      2760
     CAACTGTATGAAAAAGGTCTCTACTACGATAAAGCAGCATCTGTTTACATCCGCTCTAAG
     GTTGACATACTTTTTCCAGAGATGATGCTATTTCGTCGTAGACAAATGTAGGCGAGATTC
      Q  L  Y  E  K  G  L  Y  Y  D  K  A  A  S  V  Y  I  R  S  K>

2770      2780      2790      2800      2810      2820
     AATTGGGCAAAAGTTGGTGATCTTCTGCCCCACGTTTCTTCTCCTAAGATCCATTTGCAG
     TTAACCCGTTTTCAACCACTAGAAGACGGGGTGCAAAGAAGAGGATTCTAGGTAAACGTC
      N  W  A  K  V  G  D  L  L  P  H  V  S  S  P  K  I  H  L  Q>

2830      2840      2850      2860      2870      2880
     TATGCCAAAGCCAAGGAAGCAGATGGAAGATACAAAGAAGCTGTTGTAGCTTATGAAAAT
     ATACGGTTTCGGTTCCTTCGTCTACCTTCTATGTTTCTTCGACAACATCGAATACTTTTA
      Y  A  K  A  K  E  A  D  G  R  Y  K  E  A  V  V  A  Y  E  N>

2890      2900      2910      2920      2930      2940
     GCAAAACAGTGGCAAAGTGTAATCCGCATCTATCTGGATCACCTCAATAATCCTGAAAAA
     CGTTTTGTCACCGTTTCACATTAGGCGTAGATAGACCTAGTGGAGTTATTAGGACTTTTT
      A  K  Q  W  Q  S  V  I  R  I  Y  L  D  H  L  N  N  P  E  K>

2950      2960      2970      2980      2990      3000
     GCTGTCAATATTGTTAGAGAGACCCAGTCTCTGGATGGAGCCAAAATGGTAGCCAGGTTT
     CGACAGTTATAACAATCTCTCTGGGTCAGAGACCTACCTCGGTTTTACCATCGGTCCAAA
      A  V  N  I  V  R  E  T  Q  S  L  D  G  A  K  M  V  A  R  F>

3010      3020      3030      3040      3050      3060
     TTTCTACAGCTTGGTGACTATGGGTCTGCCATCCAGTTTCTTGTCATGTCCAAATGCAAC
     AAAGATGTCGAACCACTGATACCCAGACGGTAGGTCAAAGAACAGTACAGGTTTACGTTG
      F  L  Q  L  G  D  Y  G  S  A  I  Q  F  L  V  M  S  K  C  N>
```

Figure 1F

```
      3070      3080      3090      3100      3110      3120
AATGAAGCTTTCACACTGGCTCAGCAACACAACAAAATGGAAATCTATGCAGATATTATT
TTACTTCGAAAGTGTGACCGAGTCGTTGTGTTGTTTTACCTTTAGATACGTCTATAATAA
  N  E  A  F  T  L  Q  Q  H  N  K  M  E  I  Y  A  D  I  I>

3130      3140      3150      3160      3170      3180
GGTTCTGAAGACACTACTAATGAAGACTATCAAAGCATTGCCTTATACTTTGAAGGAGAA
CCAAGACTTCTGTGATGATTACTTCTGATAGTTTCGTAACGGAATATGAAACTTCCTCTT
  G  S  E  D  T  T  N  E  D  Y  Q  S  I  A  L  Y  F  E  G  E>

3190      3200      3210      3220      3230      3240
AAGAGATATCTTCAGGCTGGAAAATTCTTCTTGCTGTGTGGCCAATATTCACGAGCACTT
TTCTCTATAGAAGTCCGACCTTTTAAGAAGAACGACACACCGGTTATAAGTGCTCGTGAA
  K  R  Y  L  Q  A  G  K  F  F  L  C  G  Q  Y  S  R  A  L>

3250      3260      3270      3280      3290      3300
AAACACTTCCTGAAATGCCCAAGCTCGGAAGATAATGTGGCAATAGAAATGGCAATTGAA
TTTGTGAAGGACTTTACGGGTTCGAGCCTTCTATTACACCGTTATCTTTACCGTTAACTT
  K  H  F  L  K  C  P  S  S  E  D  N  V  A  I  E  M  A  I  E>

3310      3320      3330      3340      3350      3360
ACTGTTGGTCAGGCCAAAGATGAACTGCTGACCAATCAGCTGATAGACCATCTCCTGGGG
TGACAACCAGTCCGGTTTCTACTTGACGACTGGTTAGTCGACTATCTGGTAGAGGACCCC
  T  V  G  Q  A  K  D  E  L  L  T  N  Q  L  I  D  H  L  L  G>

3370      3380      3390      3400      3410      3420
GAGAACGATGGCATGCCTAAGGATGCCAAGTACCTGTTCCGCTTGTACATGGCTCTGAAG
CTCTTGCTACCGTACGGATTCCTACGGTTCATGGACAAGGCGAACATGTACCGAGACTTC
  E  N  D  G  M  P  K  D  A  K  Y  L  F  R  L  Y  M  A  L  K>

3430      3440      3450      3460      3470      3480
CAATACCGAGAAGCTGCCCAGACTGCCATCATCATTGCCAGAGAAGAGCAGTCTGCAGGC
GTTATGGCTCTTCGACGGGTCTGACGGTAGTAGTAACGGTCTCTTCTCGTCAGACGTCCG
  Q  Y  R  E  A  A  Q  T  A  I  I  I  A  R  E  E  Q  S  A  G>

3490      3500      3510      3520      3530      3540
AACTACCGGAATGCACACGATGTTCTCTTCAGTATGTATGCAGAACTGAAATCCCAGAAG
TTGATGGCCTTACGTGTGCTACAAGAGAAGTCATACATACGTCTTGACTTTAGGGTCTTC
  N  Y  R  N  A  H  D  V  L  F  S  M  Y  A  E  L  K  S  Q  K>
```

Figure 1G

```
      3550      3560      3570      3580      3590      3600
ATCAAAATTCCCTCCGAGATGGCCACCAACCTCATGATTCTGCACAGCTATATACTAGTA
TAGTTTTAAGGGAGGCTCTACCGGTGGTTGGAGTACTAAGACGTGTCGATATATGATCAT
  I  K  I  P  S  E  M  A  T  N  L  M  I  L  H  S  Y  I  L  V>

3610      3620      3630      3640      3650      3660
AAGATTCATGTTAAAAATGGAGATCACATGAAAGGGGCTCGCATGCTCATTCGGGTGGCC
TTCTAAGTACAATTTTTACCTCTAGTGTACTTTCCCCGAGCGTACGAGTAAGCCCACCGG
  K  I  H  V  K  N  G  D  H  M  K  G  A  R  M  L  I  R  V  A>

3670      3680      3690      3700      3710      3720
AACAACATCAGCAAATTTCCATCACACATTGTACCCATCCTGACGTCAACTGTGATTGAG
TTGTTGTAGTCGTTTAAAGGTAGTGTGTAACATGGGTAGGACTGCAGTTGACACTAACTC
  N  N  I  S  K  F  P  S  H  I  V  P  I  L  T  S  V  I  E>

3730      3740      3750      3760      3770      3780
TGTCACAGGGCAGGCCTGAAGAACTCTGCTTTCAGCTTCGCAGCTATGTTGATGAGGCCT
ACAGTGTCCCGTCCGGACTTCTTGAGACGAAAGTCGAAGCGTCGATACAACTACTCCGGA
  C  H  R  A  G  L  K  N  S  A  F  S  F  A  A  M  L  M  R  P>

3790      3800      3810      3820      3830      3840
GAATACCGCAGCAAAATAGATGCCAAATACAAAAAGAAGATCGAGGGAATGGTCAGGAGA
CTTATGGCGTCGTTTTATCTACGGTTTATGTTTTTCTTCTAGCTCCCTTACCAGTCCTCT
  E  Y  R  S  K  I  D  A  K  Y  K  K  K  I  E  G  M  V  R  R>

3850      3860      3870      3880      3890      3900
CCCGATATATCTGAGATAGAAGAGGCCACGACTCCATGTCCATTCTGCAAATTTCTTCTC
GGGCTATATAGACTCTATCTTCTCCGGTGCTGAGGTACAGGTAAGACGTTTAAAGAAGAG
  P  D  I  S  E  I  E  E  A  T  T  P  C  P  F  C  K  F  L  L>

3910      3920      3930      3940      3950      3960
CCAGAGTGTGAACTCCTCTGTCCTGGATGTAAAAACAGTATCCCATATTGCATTGCAACA
GGTCTCACACTTGAGGAGACAGGACCTACATTTTTGTCATAGGGTATAACGTAACGTTGT
  P  E  C  E  L  L  C  P  G  C  K  N  S  I  P  Y  C  I  A  T>

3970      3980      3990      4000      4010      4020
GGTCGACACATGTTGAAAGATGACTGGACGGTGTGTCCACATTGTGACTTCCCTGCTCTA
CCAGCTGTGTACAACTTTCTACTGACCTGCCACACAGGTGTAACACTGAAGGGACGAGAT
  G  R  H  M  L  K  D  D  W  T  V  C  P  H  C  D  F  P  A  L>
```

Figure 1H

```
        4030      4040      4050      4060      4070      4080
TACTCAGAATTGAAGATCATGCTAAACACTGAAAGCACATGTCCTATGTGTTCAGAAAGA
ATGAGTCTTAACTTCTAGTACGATTTGTGACTTTCGTGTACAGGATACACAAGTCTTTCT
 Y  S  E  L  K  I  M  L  N  T  E  S  T  C  P  M  C  S  E  R>

4090      4100      4110      4120      4130      4140
TTAAACGCTGCTCAGCTGAAAAAGATTTCAGACTGTACCCAGTACCTGCGAACGGAGGAG
AATTTGCGACGAGTCGACTTTTTCTAAAGTCTGACATGGGTCATGGACGCTTGCCTCCTC
 L  N  A  A  Q  L  K  K  I  S  D  C  T  Q  Y  L  R  T  E  E>

4150      4160      4170      4180      4190      4200
GAACTGTGATTGGCACGTGCAGATACAATGCTCCTGAGAAGACAGCATTTTCCACAGGAG
CTTGACACTAACCGTGCACGTCTATGTTACGAGGACTCTTCTGTCGTAAAAGGTGTCCTC
 E  L>
    ___>

4210      4220      4230      4240      4250      4260
GCTGTTTCCTCCCCTGGTGGATTTAAGAGACGGTCCTTTCTGGATACAGAGAAATGAAAC
CGACAAAGGAGGGGACCACCTAAATTCTCTGCCAGGAAAGACCTATGTCTCTTTACTTTG 4270      4280      4290      4300      4310      4320
AACGGTGACCTCTCCAGGTCGGCACTTTCCACTTCTGTACGGTGGCAAAACGATGACATG
TTGCCACTGGAGAGGTCCAGCCGTGAAAGGTGAAGACATGCCACCGTTTTGCTACTGTAC 4330      4340      4350      4360      4370      4380
TAACCTTGCTGTTTATTGTACTTTGTATATTATTTCCTCTTCAAAGTCTTTCTTACACAC
ATTGGAACGACAAATAACATGAAACATATAATAAAGGAGAAGTTTCAGAAAGAATGTGTG 4390      4400      4410      4420      4430      4440
TCTATCCTCTGCACTGTTAATAGTAACCTATGACATAATTGTAAATATTCAGCTTTTTGC
AGATAGGAGACGTGACAATTATCATTGGATACTGTATTAACATTTATAAGTCGAAAAACG 4450      4460      4470      4480      4490      4500
TAACTTTTGTATTTTGAAAAACTTTAAAATAAAATTGTTGACTAGAAAAAAAAAAAAAAA
ATTGAAAACATAAAACTTTTTGAAATTTTATTTTAACAACTGATCTTTTTTTTTTTTTTT
```

Figure 1I

Figure 5A
Figure 5B
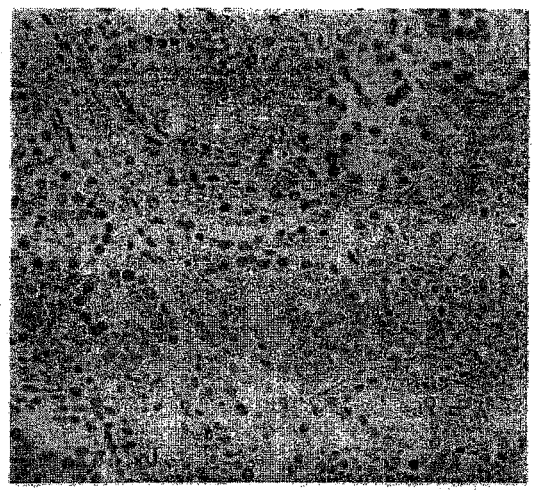
Figure 5C
Figure 5D

SEQUENCE LISTING

<160> NUMBER OF SEQ ID NOS: 10

<210> SEQ ID NO 1
<211> LENGTH: 4500
<212> TYPE: DNA
<213> ORGANISM: Homo sapien
<220> FEATURE:
<221> NAME/KEY: CDS
<222> LOCATION: (1)...(4146)
<220> FEATURE:
<221> NAME/KEY: misc_feature
<222> LOCATION: (1)...(4500)
<223> OTHER INFORMATION: Xaa=any amino acid

<400> SEQUENCE: 1

```
cac tcg ctg att ggt cgc tgc tcg cgc ggt ctc ctg ggt gac ggg aac        48
His Ser Leu Ile Gly Arg Cys Ser Arg Gly Leu Leu Gly Asp Gly Asn
1               5                   10                  15 gcg gta gcc tgc ttg gtg gag acc ggg tgc gcc tgc gta ctt cat agt        96
Ala Val Ala Cys Leu Val Glu Thr Gly Cys Ala Cys Val Leu His Ser
            20                  25                  30 tcg cgt agc ggc tcg agc gtg gag atg aag cgt att ttc tca ctg cta       144
Ser Arg Ser Gly Ser Ser Val Glu Met Lys Arg Ile Phe Ser Leu Leu
        35                  40                  45 gaa aag act tgg ctt ggc gca cca ata cag ttt gcc tgg caa aaa aca       192
Glu Lys Thr Trp Leu Gly Ala Pro Ile Gln Phe Ala Trp Gln Lys Thr
    50                  55                  60 tca gga aac tac ctt gca gta aca gga gct gat tat att gtg aaa atc       240
Ser Gly Asn Tyr Leu Ala Val Thr Gly Ala Asp Tyr Ile Val Lys Ile
65                  70                  75                  80 ttt gat cgc cat ggt caa aaa aga agt gaa att aac tta cct ggt aac       288
Phe Asp Arg His Gly Gln Lys Arg Ser Glu Ile Asn Leu Pro Gly Asn
                85                  90                  95 tgt gtt gcc atg gat tgg gat aaa gat gga gat gtc cta gca gtg att       336
Cys Val Ala Met Asp Trp Asp Lys Asp Gly Asp Val Leu Ala Val Ile
            100                 105                 110 gct gag aaa tct agc tgc att tat ctt tgg gat gcc aac aca aat aag       384
Ala Glu Lys Ser Ser Cys Ile Tyr Leu Trp Asp Ala Asn Thr Asn Lys
        115                 120                 125
```

| | |
|---|---|
| acc agc cag tta gac aat ggc atg agg gat caa atg tct ttc ctt ctt<br>Thr Ser Gln Leu Asp Asn Gly Met Arg Asp Gln Met Ser Phe Leu Leu<br>130                           135                        140 | 432 |
| tgg tca aaa gtt gga agt ttc ctg gct gtt gga act gtt aaa gga aat<br>Trp Ser Lys Val Gly Ser Phe Leu Ala Val Gly Thr Val Lys Gly Asn<br>145                    150                    155                    160 | 480 |
| ttg stt att tat aat cat cag aca tct cga aag att cct gtc ctt gga<br>Leu Xaa Ile Tyr Asn His Gln Thr Ser Arg Lys Ile Pro Val Leu Gly<br>                    165                    170                    175 | 528 |
| aaa cat act aag aga atc act tgt gga tgt tgg aat gca gaa aat ctg<br>Lys His Thr Lys Arg Ile Thr Cys Gly Cys Trp Asn Ala Glu Asn Leu<br>                        180                    185                    190 | 576 |
| cyt gct tta ggt ggt gaa gat aaa atg att aca gtt agt aat cag gaa<br>Xaa Ala Leu Gly Gly Glu Asp Lys Met Ile Thr Val Ser Asn Gln Glu<br>              195                    200                    205 | 624 |
| ggt gac acg ata aga cag aca caa gtg aga tca gag cct akc aac atg<br>Gly Asp Thr Ile Arg Gln Thr Gln Val Arg Ser Glu Pro Xaa Asn Met<br>210                           215                    220 | 672 |
| cag ttt ttc ttg atg aag atg gat gac cga acc tct gct gct gaa agc<br>Gln Phe Phe Leu Met Lys Met Asp Asp Arg Thr Ser Ala Ala Glu Ser<br>225                           230                    235                    240 | 720 |
| atg ata agt gtg gtg ctt ggc aag aaa act ttg ttt ttt tta aat ctg<br>Met Ile Ser Val Val Leu Gly Lys Lys Thr Leu Phe Phe Leu Asn Leu<br>                    245                    250                    255 | 768 |
| aat gaa cca gat aac cca gct gat ctt gaa ttt cag cag gac ttt ggc<br>Asn Glu Pro Asp Asn Pro Ala Asp Leu Glu Phe Gln Gln Asp Phe Gly<br>                        260                    265                    270 | 816 |
| aac att gtc tgc tat aat tgg tat ggt gat ggc cgc atc atg att ggt<br>Asn Ile Val Cys Tyr Asn Trp Tyr Gly Asp Gly Arg Ile Met Ile Gly<br>              275                    280                    285 | 864 |
| ttt tca tgt gga cat ttt gtg gtc att tct act cat act gga gag ctt<br>Phe Ser Cys Gly His Phe Val Val Ile Ser Thr His Thr Gly Glu Leu<br>290                           295                    300 | 912 |
| ggt caa gag ata ttt cag gct cgt aac cat aaa gat aat cta acc agc<br>Gly Gln Glu Ile Phe Gln Ala Arg Asn His Lys Asp Asn Leu Thr Ser<br>305                         310                    315                    320 | 960 |
| att gca gta tca cag act ctt aac aaa gtt gct aca tgt gga gat aac<br>Ile Ala Val Ser Gln Thr Leu Asn Lys Val Ala Thr Cys Gly Asp Asn<br>              325                    330                    335 | 1008 |
| tgc att aaa atc caa gac ttg gtt gac tta aaa gac atg tat gtt ata<br>Cys Ile Lys Ile Gln Asp Leu Val Asp Leu Lys Asp Met Tyr Val Ile<br>                    340                    345                    350 | 1056 |
| ctc aac ctg gat gag gaa aat aaa gga ttg ggt acc ttg tcc tgg act<br>Leu Asn Leu Asp Glu Glu Asn Lys Gly Leu Gly Thr Leu Ser Trp Thr<br>              355                    360                    365 | 1104 |
| gat gat ggc cag ttg cta gca ctc tct acc caa agg ggc tca ctt cat<br>Asp Asp Gly Gln Leu Leu Ala Leu Ser Thr Gln Arg Gly Ser Leu His<br>                    370                    375                    380 | 1152 |
| gtt ttc ctg acc aag ctt ccc ata ctt ggg gat gcc tgc agc aca agg<br>Val Phe Leu Thr Lys Leu Pro Ile Leu Gly Asp Ala Cys Ser Thr Arg<br>385                           390                    395                    400 | 1200 |
| att gcc tat ctc acc tcc ctc ctt gaa gtc acc gta gcc aac cct gtt<br>Ile Ala Tyr Leu Thr Ser Leu Leu Glu Val Thr Val Ala Asn Pro Val<br>                    405                    410                    415 | 1248 |
| gaa gga gag cta cca atc aca gtt tct gtt gat gtg gaa ccc aac ttt<br>Glu Gly Glu Leu Pro Ile Thr Val Ser Val Asp Val Glu Pro Asn Phe<br>              420                    425                    430 | 1296 |
| gtg gca gta ggt ctt tat cat ctg gct gta gga atg aat aat cga gct<br>Val Ala Val Gly Leu Tyr His Leu Ala Val Gly Met Asn Asn Arg Ala<br>                    435                    440                    445 | 1344 |

-continued

| | | |
|---|---|---|
| tgg ttt tat gtc ctt gga gaa aat gct gtg aaa aaa ttg aaa gat atg<br>Trp Phe Tyr Val Leu Gly Glu Asn Ala Val Lys Lys Leu Lys Asp Met<br>    450                             455                      460 | 1392 |
| gag tat ctg gga aca gta gcc agt att tgc ctt cat tct gac tat gct<br>Glu Tyr Leu Gly Thr Val Ala Ser Ile Cys Leu His Ser Asp Tyr Ala<br>465                        470                      475                  480 | 1440 |
| gct gca ctt ttt gaa ggc aaa gtc cag tta cat ttg ata gaa agc gaa<br>Ala Ala Leu Phe Glu Gly Lys Val Gln Leu His Leu Ile Glu Ser Glu<br>                    485                      490                      495 | 1488 |
| atc ttg gat gct caa gaa gaa cgt gag act cgg ctt ttc cca gca gtg<br>Ile Leu Asp Ala Gln Glu Glu Arg Glu Thr Arg Leu Phe Pro Ala Val<br>                500                      505                      510 | 1536 |
| gat gat aag tgc cgt atc tta tgc cat gcc tta act agt gat ttc ctc<br>Asp Asp Lys Cys Arg Ile Leu Cys His Ala Leu Thr Ser Asp Phe Leu<br>            515                      520                      525 | 1584 |
| atc tat ggt aca gat act ggt gtc gtt cag tat ttc tac att gaa gac<br>Ile Tyr Gly Thr Asp Thr Gly Val Val Gln Tyr Phe Tyr Ile Glu Asp<br>          530                      535                      540 | 1632 |
| tgg caa ttc gtt aat gat tat cga cat cct gtc agt gtg aaa aag att<br>Trp Gln Phe Val Asn Asp Tyr Arg His Pro Val Ser Val Lys Lys Ile<br>545                      550                      555                      560 | 1680 |
| ttt ccc gac cca aat ggg acc aga tta gtt ttc att gat gaa aaa agt<br>Phe Pro Asp Pro Asn Gly Thr Arg Leu Val Phe Ile Asp Glu Lys Ser<br>                    565                      570                      575 | 1728 |
| gat gga ttt gtt tac tgt cca gtc aat gac gct acc tat gag att cca<br>Asp Gly Phe Val Tyr Cys Pro Val Asn Asp Ala Thr Tyr Glu Ile Pro<br>            580                      585                      590 | 1776 |
| gat ttt tca cca acc att aaa ggt gtt ctt tgg gaa aac tgg cca atg<br>Asp Phe Ser Pro Thr Ile Lys Gly Val Leu Trp Glu Asn Trp Pro Met<br>                595                      600                      605 | 1824 |
| gat aaa ggt gta ttt att gct tat gat gat gat aag gtg tac act tat<br>Asp Lys Gly Val Phe Ile Ala Tyr Asp Asp Asp Lys Val Tyr Thr Tyr<br>          610                      615                      620 | 1872 |
| gtc ttt cac aag gac act ata caa gga gcc aag gtt att ttg gct ggt<br>Val Phe His Lys Asp Thr Ile Gln Gly Ala Lys Val Ile Leu Ala Gly<br>625                      630                      635                      640 | 1920 |
| agc acc aaa gtt cct ttt gct cat aaa cct ttg ctg cta tat aat gga<br>Ser Thr Lys Val Pro Phe Ala His Lys Pro Leu Leu Leu Tyr Asn Gly<br>                    645                      650                      655 | 1968 |
| gag ctg acc tgc caa aca cag agt gga aaa gta aac aac atc tac ctt<br>Glu Leu Thr Cys Gln Thr Gln Ser Gly Lys Val Asn Asn Ile Tyr Leu<br>                660                      665                      670 | 2016 |
| agc acc cat ggc ttt ctc agc aac tta aaa gat asg ggg cct gac gaa<br>Ser Thr His Gly Phe Leu Ser Asn Leu Lys Asp Xaa Gly Pro Asp Glu<br>          675                      680                      685 | 2064 |
| ctg aga cca atg ctg gca cac aat tta atg cta aag agg ttt tct gat<br>Leu Arg Pro Met Leu Ala His Asn Leu Met Leu Lys Arg Phe Ser Asp<br>          690                      695                      700 | 2112 |
| gct tgg gaa atg tgc agg att ctg aat gat gag gct gcc tgg aat gag<br>Ala Trp Glu Met Cys Arg Ile Leu Asn Asp Glu Ala Ala Trp Asn Glu<br>705                      710                      715                      720 | 2160 |
| ttg gcc aga gct tgt cta cat cac atg gaa gtg gag ttt gca atc cgt<br>Leu Ala Arg Ala Cys Leu His His Met Glu Val Glu Phe Ala Ile Arg<br>                725                      730                      735 | 2208 |
| gtt tat cgg aga att gga aat gtt ggc ata gtg atg tcc ttg gaa caa<br>Val Tyr Arg Arg Ile Gly Asn Val Gly Ile Val Met Ser Leu Glu Gln<br>                    740                      745                      750 | 2256 |
| ata aag gga ata gag gac tac aat ctt ttg gca gga cac ctt gcc atg<br>Ile Lys Gly Ile Glu Asp Tyr Asn Leu Leu Ala Gly His Leu Ala Met<br>          755                      760                      765 | 2304 |

```
                                                          -continued
ttt acc aac gat tat aac ctg gct cag gac ttg tac ctt gca tcc agc         2352
Phe Thr Asn Asp Tyr Asn Leu Ala Gln Asp Leu Tyr Leu Ala Ser Ser
    770                 775                 780 tgt cct att gct gcc ctg gag atg aga agg gat tta cag cat tgg gac         2400
Cys Pro Ile Ala Ala Leu Glu Met Arg Arg Asp Leu Gln His Trp Asp
785                 790                 795                 800 agt gct cta caa ctg gca aag cat ttg gcc cca gac cag ata cct ttt         2448
Ser Ala Leu Gln Leu Ala Lys His Leu Ala Pro Asp Gln Ile Pro Phe
                805                 810                 815 ata tca aaa gaa tat gct att cag ctt gaa ttc gcg ggt gat tat gta         2496
Ile Ser Lys Glu Tyr Ala Ile Gln Leu Glu Phe Ala Gly Asp Tyr Val
            820                 825                 830 aat gct ttg gct cat tat gag aaa gga ata aca ggt gat aat aag gaa         2544
Asn Ala Leu Ala His Tyr Glu Lys Gly Ile Thr Gly Asp Asn Lys Glu
        835                 840                 845 cat gat gaa gct tgt ctg gct gga gtg gcc cag atg tcc ata aga atg         2592
His Asp Glu Ala Cys Leu Ala Gly Val Ala Gln Met Ser Ile Arg Met
    850                 855                 860 gga gac ata cgt cga ggg gtt aac caa gcc ctc aag cat ccc agc agg         2640
Gly Asp Ile Arg Arg Gly Val Asn Gln Ala Leu Lys His Pro Ser Arg
865                 870                 875                 880 gtc ctt aaa aga gac tgt gga gcc ata ttg gag aat atg aag caa ttt         2688
Val Leu Lys Arg Asp Cys Gly Ala Ile Leu Glu Asn Met Lys Gln Phe
                885                 890                 895 tca gaa gcg gcc caa ctg tat gaa aaa ggt ctc tac tac gat aaa gca         2736
Ser Glu Ala Ala Gln Leu Tyr Glu Lys Gly Leu Tyr Tyr Asp Lys Ala
            900                 905                 910 gca tct gtt tac atc cgc tct aag aat tgg gca aaa gtt ggt gat ctt         2784
Ala Ser Val Tyr Ile Arg Ser Lys Asn Trp Ala Lys Val Gly Asp Leu
        915                 920                 925 ctg ccc cac gtt tct tct cct aag atc cat ttg cag tat gcc aaa gcc         2832
Leu Pro His Val Ser Ser Pro Lys Ile His Leu Gln Tyr Ala Lys Ala
    930                 935                 940 aag gaa gca gat gga aga tac aaa gaa gct gtt gta gct tat gaa aat         2880
Lys Glu Ala Asp Gly Arg Tyr Lys Glu Ala Val Val Ala Tyr Glu Asn
945                 950                 955                 960 gca aaa cag tgg caa agt gta atc cgc atc tat ctg gat cac ctc aat         2928
Ala Lys Gln Trp Gln Ser Val Ile Arg Ile Tyr Leu Asp His Leu Asn
                965                 970                 975 aat cct gaa aaa gct gtc aat att gtt aga gag acc cag tct ctg gat         2976
Asn Pro Glu Lys Ala Val Asn Ile Val Arg Glu Thr Gln Ser Leu Asp
            980                 985                 990 gga gcc aaa atg gta gcc agg ttt ttt cta cag ctt ggt gac tat ggg         3024
Gly Ala Lys Met Val Ala Arg Phe Phe Leu Gln Leu Gly Asp Tyr Gly
        995                 1000                1005 tct gcc atc cag ttt ctt gtc atg tcc aaa tgc aac aat gaa gct ttc         3072
Ser Ala Ile Gln Phe Leu Val Met Ser Lys Cys Asn Asn Glu Ala Phe
    1010                1015                1020 aca ctg gct cag caa cac aac aaa atg gaa atc tat gca gat att att         3120
Thr Leu Ala Gln Gln His Asn Lys Met Glu Ile Tyr Ala Asp Ile Ile
1025                1030                1035                1040 ggt tct gaa gac act act aat gaa gac tat caa agc att gcc tta tac         3168
Gly Ser Glu Asp Thr Thr Asn Glu Asp Tyr Gln Ser Ile Ala Leu Tyr
                1045                1050                1055 ttt gaa gga gaa aag aga tat ctt cag gct gga aaa ttc ttc ttg ctg         3216
Phe Glu Gly Glu Lys Arg Tyr Leu Gln Ala Gly Lys Phe Phe Leu Leu
            1060                1065                1070 tgt ggc caa tat tca cga gca ctt aaa cac ttc ctg aaa tgc cca agc         3264
Cys Gly Gln Tyr Ser Arg Ala Leu Lys His Phe Leu Lys Cys Pro Ser
        1075                1080                1085
```

```
tcg gaa gat aat gtg gca ata gaa atg gca att gaa act gtt ggt cag      3312
Ser Glu Asp Asn Val Ala Ile Glu Met Ala Ile Glu Thr Val Gly Gln
    1090                1095                1100 gcc aaa gat gaa ctg ctg acc aat cag ctg ata gac cat ctc ctg ggg      3360
Ala Lys Asp Glu Leu Leu Thr Asn Gln Leu Ile Asp His Leu Leu Gly
1105                1110                1115                1120 gag aac gat ggc atg cct aag gat gcc aag tac ctg ttc cgc ttg tac      3408
Glu Asn Asp Gly Met Pro Lys Asp Ala Lys Tyr Leu Phe Arg Leu Tyr
                1125                1130                1135 atg gct ctg aag caa tac cga gaa gct gcc cag act gcc atc atc att      3456
Met Ala Leu Lys Gln Tyr Arg Glu Ala Ala Gln Thr Ala Ile Ile Ile
            1140                1145                1150 gcc aga gaa gag cag tct gca ggc aac tac cgg aat gca cac gat gtt      3504
Ala Arg Glu Glu Gln Ser Ala Gly Asn Tyr Arg Asn Ala His Asp Val
        1155                1160                1165 ctc ttc agt atg tat gca gaa ctg aaa tcc cag aag atc aaa att ccc      3552
Leu Phe Ser Met Tyr Ala Glu Leu Lys Ser Gln Lys Ile Lys Ile Pro
    1170                1175                1180 tcc gag atg gcc acc aac ctc atg att ctg cac agc tat ata cta gta      3600
Ser Glu Met Ala Thr Asn Leu Met Ile Leu His Ser Tyr Ile Leu Val
1185                1190                1195                1200 aag att cat gtt aaa aat gga gat cac atg aaa ggg gct cgc atg ctc      3648
Lys Ile His Val Lys Asn Gly Asp His Met Lys Gly Ala Arg Met Leu
                1205                1210                1215 att cgg gtg gcc aac aac atc agc aaa ttt cca tca cac att gta ccc      3696
Ile Arg Val Ala Asn Asn Ile Ser Lys Phe Pro Ser His Ile Val Pro
            1220                1225                1230 atc ctg acg tca act gtg att gag tgt cac agg gca ggc ctg aag aac      3744
Ile Leu Thr Ser Thr Val Ile Glu Cys His Arg Ala Gly Leu Lys Asn
        1235                1240                1245 tct gct ttc agc ttc gca gct atg ttg atg agg cct gaa tac cgc agc      3792
Ser Ala Phe Ser Phe Ala Ala Met Leu Met Arg Pro Glu Tyr Arg Ser
    1250                1255                1260 aaa ata gat gcc aaa tac aaa aag aag atc gag gga atg gtc agg aga      3840
Lys Ile Asp Ala Lys Tyr Lys Lys Lys Ile Glu Gly Met Val Arg Arg
1265                1270                1275                1280 ccc gat ata tct gag ata gaa gag gcc acg act cca tgt cca ttc tgc      3888
Pro Asp Ile Ser Glu Ile Glu Glu Ala Thr Thr Pro Cys Pro Phe Cys
                1285                1290                1295 aaa ttt ctt ctc cca gag tgt gaa ctc ctc tgt cct gga tgt aaa aac      3936
Lys Phe Leu Leu Pro Glu Cys Glu Leu Leu Cys Pro Gly Cys Lys Asn
            1300                1305                1310 agt atc cca tat tgc att gca aca ggt cga cac atg ttg aaa gat gac      3984
Ser Ile Pro Tyr Cys Ile Ala Thr Gly Arg His Met Leu Lys Asp Asp
        1315                1320                1325 tgg acg gtg tgt cca cat tgt gac ttc cct gct cta tac tca gaa ttg      4032
Trp Thr Val Cys Pro His Cys Asp Phe Pro Ala Leu Tyr Ser Glu Leu
    1330                1335                1340 aag atc atg cta aac act gaa agc aca tgt cct atg tgt tca gaa aga      4080
Lys Ile Met Leu Asn Thr Glu Ser Thr Cys Pro Met Cys Ser Glu Arg
1345                1350                1355                1360 tta aac gct gct cag ctg aaa aag att tca gac tgt acc cag tac ctg      4128
Leu Asn Ala Ala Gln Leu Lys Lys Ile Ser Asp Cys Thr Gln Tyr Leu
                1365                1370                1375 cga acg gag gag gaa ctg tgattggcac gtgcagatac aatgctcctg             4176
Arg Thr Glu Glu Glu Leu
            1380 agaagacagc attttccaca ggaggctgtt tcctcccctg gtggatttaa gagacggtcc    4236 tttctggata cagagaaatg aaacaacggt gacctctcca ggtcggcact ttccacttct   4296
```

```
gtacggtggc aaaacgatga catgtaacct tgctgtttat tgtactttgt atattatttc    4356
ctcttcaaag tctttcttac acactctatc ctctgcactg ttaatagtaa cctatgacat    4416
aattgtaaat attcagcttt tgctaactt  ttgtattttg aaaaacttta aataaaatt     4476 gttgactaga aaaaaaaaaa aaaa                                           4500
```

<210> SEQ ID NO 2
<211> LENGTH: 1382
<212> TYPE: PRT
<213> ORGANISM: Homo sapien
<220> FEATURE:
<221> NAME/KEY: VARIANT
<222> LOCATION: (1)...(1382)
<223> OTHER INFORMATION: Xaa = Any Amino Acid

<400> SEQUENCE: 2

```
His Ser Leu Ile Gly Arg Cys Ser Arg Gly Leu Leu Gly Asp Gly Asn
 1               5                  10                  15

Ala Val Ala Cys Leu Val Glu Thr Gly Cys Ala Cys Val Leu His Ser
            20                  25                  30

Ser Arg Ser Gly Ser Ser Val Glu Met Lys Arg Ile Phe Ser Leu Leu
        35                  40                  45

Glu Lys Thr Trp Leu Gly Ala Pro Ile Gln Phe Ala Trp Gln Lys Thr
    50                  55                  60

Ser Gly Asn Tyr Leu Ala Val Thr Gly Ala Asp Tyr Ile Val Lys Ile
65                  70                  75                  80

Phe Asp Arg His Gly Gln Lys Arg Ser Glu Ile Asn Leu Pro Gly Asn
                85                  90                  95

Cys Val Ala Met Asp Trp Asp Lys Asp Gly Asp Val Leu Ala Val Ile
            100                 105                 110

Ala Glu Lys Ser Ser Cys Ile Tyr Leu Trp Asp Ala Asn Thr Asn Lys
        115                 120                 125

Thr Ser Gln Leu Asp Asn Gly Met Arg Asp Gln Met Ser Phe Leu Leu
    130                 135                 140

Trp Ser Lys Val Gly Ser Phe Leu Ala Val Gly Thr Val Lys Gly Asn
145                 150                 155                 160

Leu Xaa Ile Tyr Asn His Gln Thr Ser Arg Lys Ile Pro Val Leu Gly
                165                 170                 175

Lys His Thr Lys Arg Ile Thr Cys Gly Cys Trp Asn Ala Glu Asn Leu
            180                 185                 190

Xaa Ala Leu Gly Gly Glu Asp Lys Met Ile Thr Val Ser Asn Gln Glu
        195                 200                 205

Gly Asp Thr Ile Arg Gln Thr Gln Val Arg Ser Glu Pro Xaa Asn Met
    210                 215                 220

Gln Phe Phe Leu Met Lys Met Asp Asp Arg Thr Ser Ala Ala Glu Ser
225                 230                 235                 240

Met Ile Ser Val Val Leu Gly Lys Lys Thr Leu Phe Phe Leu Asn Leu
                245                 250                 255

Asn Glu Pro Asp Asn Pro Ala Asp Leu Glu Phe Gln Gln Asp Phe Gly
            260                 265                 270

Asn Ile Val Cys Tyr Asn Trp Tyr Gly Asp Gly Arg Ile Met Ile Gly
        275                 280                 285

Phe Ser Cys Gly His Phe Val Val Ile Ser Thr His Thr Gly Glu Leu
    290                 295                 300

Gly Gln Glu Ile Phe Gln Ala Arg Asn His Lys Asp Asn Leu Thr Ser
305                 310                 315                 320
```

```
Ile Ala Val Ser Gln Thr Leu Asn Lys Val Ala Thr Cys Gly Asp Asn
            325                 330                 335

Cys Ile Lys Ile Gln Asp Leu Val Asp Leu Lys Asp Met Tyr Val Ile
            340                 345                 350

Leu Asn Leu Asp Glu Glu Asn Lys Gly Leu Gly Thr Leu Ser Trp Thr
            355                 360                 365

Asp Asp Gly Gln Leu Leu Ala Leu Ser Thr Gln Arg Gly Ser Leu His
            370                 375                 380

Val Phe Leu Thr Lys Leu Pro Ile Leu Gly Asp Ala Cys Ser Thr Arg
385                 390                 395                 400

Ile Ala Tyr Leu Thr Ser Leu Leu Glu Val Thr Val Ala Asn Pro Val
            405                 410                 415

Glu Gly Glu Leu Pro Ile Thr Val Ser Val Asp Val Glu Pro Asn Phe
            420                 425                 430

Val Ala Val Gly Leu Tyr His Leu Ala Val Gly Met Asn Asn Arg Ala
            435                 440                 445

Trp Phe Tyr Val Leu Gly Glu Asn Ala Val Lys Lys Leu Lys Asp Met
            450                 455                 460

Glu Tyr Leu Gly Thr Val Ala Ser Ile Cys Leu His Ser Asp Tyr Ala
465                 470                 475                 480

Ala Ala Leu Phe Glu Gly Lys Val Gln Leu His Leu Ile Glu Ser Glu
            485                 490                 495

Ile Leu Asp Ala Gln Glu Glu Arg Glu Thr Arg Leu Phe Pro Ala Val
            500                 505                 510

Asp Asp Lys Cys Arg Ile Leu Cys His Ala Leu Thr Ser Asp Phe Leu
            515                 520                 525

Ile Tyr Gly Thr Asp Thr Gly Val Val Gln Tyr Phe Tyr Ile Glu Asp
            530                 535                 540

Trp Gln Phe Val Asn Asp Tyr Arg His Pro Val Ser Val Lys Lys Ile
545                 550                 555                 560

Phe Pro Asp Pro Asn Gly Thr Arg Leu Val Phe Ile Asp Glu Lys Ser
            565                 570                 575

Asp Gly Phe Val Tyr Cys Pro Val Asn Asp Ala Thr Tyr Glu Ile Pro
            580                 585                 590

Asp Phe Ser Pro Thr Ile Lys Gly Val Leu Trp Glu Asn Trp Pro Met
            595                 600                 605

Asp Lys Gly Val Phe Ile Ala Tyr Asp Asp Asp Lys Val Tyr Thr Tyr
            610                 615                 620

Val Phe His Lys Asp Thr Ile Gln Gly Ala Lys Val Ile Leu Ala Gly
625                 630                 635                 640

Ser Thr Lys Val Pro Phe Ala His Lys Pro Leu Leu Leu Tyr Asn Gly
            645                 650                 655

Glu Leu Thr Cys Gln Thr Gln Ser Gly Lys Val Asn Asn Ile Tyr Leu
            660                 665                 670

Ser Thr His Gly Phe Leu Ser Asn Leu Lys Asp Xaa Gly Pro Asp Glu
            675                 680                 685

Leu Arg Pro Met Leu Ala His Asn Leu Met Leu Lys Arg Phe Ser Asp
            690                 695                 700

Ala Trp Glu Met Cys Arg Ile Leu Asn Asp Glu Ala Ala Trp Asn Glu
705                 710                 715                 720

Leu Ala Arg Ala Cys Leu His His Met Glu Val Glu Phe Ala Ile Arg
            725                 730                 735

Val Tyr Arg Arg Ile Gly Asn Val Gly Ile Val Met Ser Leu Glu Gln
            740                 745                 750
```

-continued

Ile Lys Gly Ile Glu Asp Tyr Asn Leu Leu Ala Gly His Leu Ala Met
       755                 760                 765

Phe Thr Asn Asp Tyr Asn Leu Ala Gln Asp Leu Tyr Leu Ala Ser Ser
       770                 775                 780

Cys Pro Ile Ala Ala Leu Glu Met Arg Arg Asp Leu Gln His Trp Asp
785                 790                 795                 800

Ser Ala Leu Gln Leu Ala Lys His Leu Ala Pro Asp Gln Ile Pro Phe
               805                 810                 815

Ile Ser Lys Glu Tyr Ala Ile Gln Leu Glu Phe Ala Gly Asp Tyr Val
           820                 825                 830

Asn Ala Leu Ala His Tyr Glu Lys Gly Ile Thr Gly Asp Asn Lys Glu
               835                 840                 845

His Asp Glu Ala Cys Leu Ala Gly Val Ala Gln Met Ser Ile Arg Met
       850                 855                 860

Gly Asp Ile Arg Arg Gly Val Asn Gln Ala Leu Lys His Pro Ser Arg
865                 870                 875                 880

Val Leu Lys Arg Asp Cys Gly Ala Ile Leu Glu Asn Met Lys Gln Phe
               885                 890                 895

Ser Glu Ala Ala Gln Leu Tyr Glu Lys Gly Leu Tyr Tyr Asp Lys Ala
           900                 905                 910

Ala Ser Val Tyr Ile Arg Ser Lys Asn Trp Ala Lys Val Gly Asp Leu
           915                 920                 925

Leu Pro His Val Ser Ser Pro Lys Ile His Leu Gln Tyr Ala Lys Ala
       930                 935                 940

Lys Glu Ala Asp Gly Arg Tyr Lys Glu Ala Val Val Ala Tyr Glu Asn
945                 950                 955                 960

Ala Lys Gln Trp Gln Ser Val Ile Arg Ile Tyr Leu Asp His Leu Asn
               965                 970                 975

Asn Pro Glu Lys Ala Val Asn Ile Val Arg Glu Thr Gln Ser Leu Asp
           980                 985                 990

Gly Ala Lys Met Val Ala Arg Phe Phe Leu Gln Leu Gly Asp Tyr Gly
           995                 1000                1005

Ser Ala Ile Gln Phe Leu Val Met Ser Lys Cys Asn Asn Glu Ala Phe
       1010                1015                1020

Thr Leu Ala Gln Gln His Asn Lys Met Glu Ile Tyr Ala Asp Ile Ile
1025                1030                1035                1040

Gly Ser Glu Asp Thr Thr Asn Glu Asp Tyr Gln Ser Ile Ala Leu Tyr
               1045                1050                1055

Phe Glu Gly Glu Lys Arg Tyr Leu Gln Ala Gly Lys Phe Phe Leu Leu
           1060                1065                1070

Cys Gly Gln Tyr Ser Arg Ala Leu Lys His Phe Leu Lys Cys Pro Ser
           1075                1080                1085

Ser Glu Asp Asn Val Ala Ile Glu Met Ala Ile Glu Thr Val Gly Gln
       1090                1095                1100

Ala Lys Asp Glu Leu Leu Thr Asn Gln Leu Ile Asp His Leu Leu Gly
1105                1110                1115                1120

Glu Asn Asp Gly Met Pro Lys Asp Ala Lys Tyr Leu Phe Arg Leu Tyr
               1125                1130                1135

Met Ala Leu Lys Gln Tyr Arg Glu Ala Ala Gln Thr Ala Ile Ile Ile
           1140                1145                1150

Ala Arg Glu Glu Gln Ser Ala Gly Asn Tyr Arg Asn Ala His Asp Val
           1155                1160                1165

Leu Phe Ser Met Tyr Ala Glu Leu Lys Ser Gln Lys Ile Lys Ile Pro

```
                1170                1175                1180
Ser Glu Met Ala Thr Asn Leu Met Ile Leu His Ser Tyr Ile Leu Val
1185                1190                1195                1200

Lys Ile His Val Lys Asn Gly Asp His Met Lys Gly Ala Arg Met Leu
                1205                1210                1215

Ile Arg Val Ala Asn Asn Ile Ser Lys Phe Pro Ser His Ile Val Pro
                1220                1225                1230

Ile Leu Thr Ser Thr Val Ile Glu Cys His Arg Ala Gly Leu Lys Asn
                1235                1240                1245

Ser Ala Phe Ser Phe Ala Ala Met Leu Met Arg Pro Glu Tyr Arg Ser
                1250                1255                1260

Lys Ile Asp Ala Lys Tyr Lys Lys Ile Glu Gly Met Val Arg Arg
1265                1270                1275                1280

Pro Asp Ile Ser Glu Ile Glu Ala Thr Thr Pro Cys Pro Phe Cys
                1285                1290                1295

Lys Phe Leu Leu Pro Glu Cys Glu Leu Leu Cys Pro Gly Cys Lys Asn
                1300                1305                1310

Ser Ile Pro Tyr Cys Ile Ala Thr Gly Arg His Met Leu Lys Asp Asp
                1315                1320                1325

Trp Thr Val Cys Pro His Cys Asp Phe Pro Ala Leu Tyr Ser Glu Leu
                1330                1335                1340

Lys Ile Met Leu Asn Thr Glu Ser Thr Cys Pro Met Cys Ser Glu Arg
1345                1350                1355                1360

Leu Asn Ala Ala Gln Leu Lys Lys Ile Ser Asp Cys Thr Gln Tyr Leu
                1365                1370                1375

Arg Thr Glu Glu Glu Leu
                1380

<210> SEQ ID NO 3
<211> LENGTH: 29
<212> TYPE: DNA
<213> ORGANISM: Homo sapien

<400> SEQUENCE: 3 ttttgtatt ggcatctatt ttgctgcgg                                    29

<210> SEQ ID NO 4
<211> LENGTH: 24
<212> TYPE: DNA
<213> ORGANISM: Homo sapien

<400> SEQUENCE: 4
tgcagaatgg acatggagtc gtgg                                        24

<210> SEQ ID NO 5
<211> LENGTH: 22
<212> TYPE: DNA
<213> ORGANISM: Homo sapiens

<400> SEQUENCE: 5
gctgggatgc ttgagggctt gg                                          22

<210> SEQ ID NO 6
<211> LENGTH: 24
<212> TYPE: DNA
<213> ORGANISM: Homo sapiens

<400> SEQUENCE: 6
aaggaccctg ctgggatgct tgag                                        24
```

```
<210> SEQ ID NO 7
<211> LENGTH: 25
<212> TYPE: DNA
<213> ORGANISM: Homo sapiens

<400> SEQUENCE: 7
tgaagaactc tgctttcagc ttcga                                            25

<210> SEQ ID NO 8
<211> LENGTH: 25
<212> TYPE: DNA
<213> ORGANISM: Homo sapiens

<400> SEQUENCE: 8
aggaaacagc ctcctgtgga aaatg                                            25

<210> SEQ ID NO 9
<211> LENGTH: 24
<212> TYPE: DNA
<213> ORGANISM: Homo sapiens

<400> SEQUENCE: 9
acgtgcagat acaatgctcc tgag                                             24

<210> SEQ ID NO 10
<211> LENGTH: 21
<212> TYPE: DNA
<213> ORGANISM: Homo sapiens

<400> SEQUENCE: 10
catgtcatcg ttttgccacc g                                                21
```

PROSTATE-SPECIFIC POLYPEPTIDE PAMP AND ENCODING NUCLEIC ACID MOLECULES

CROSS-REFERENCE TO RELATED APPLICATIONS

This application is a continuation of U.S. application Ser. No. 09/729,653, filed Dec. 4, 2000, the entire contents of which is incorporated herein by reference.

BACKGROUND OF THE INVENTION

This invention relates generally to cancer and, more specifically, to a prostate-specific gene that can be used to diagnose and treat prostate cancer, including advanced or metastatic prostate cancer.

Cancer is currently the second leading cause of mortality in the United States. However, it is estimated that by the year 2000 cancer will surpass heart disease and become the leading cause of death in the United States. Prostate cancer is the most common non-cutaneous cancer in the United States and the second leading cause of male cancer mortality.

Cancerous tumors result when a cell escapes from its normal growth regulatory mechanisms and proliferates in an uncontrolled fashion. As a result of such uncontrolled proliferation, cancerous tumors usually invade neighboring tissues and spread by lymph or blood stream to create secondary or metastatic growths in other tissues. If untreated, cancerous tumors follow a fatal course. Prostate cancer, due to its slow growth profile, is an excellent candidate for early detection and therapeutic intervention.

During the last decade, most advances in prostate cancer research have focused on prostate specific antigen (PSA), a member of the serine protease family that exhibits a prostate-specific expression profile. Serum PSA remains the most widely used tumor marker for monitoring prostate cancer, but its specificity is limited by a high frequency of falsely elevated values in men with benign prostatic hyperplasia (BPH). Other biomarkers of prostate cancer progression have proven to be of limited clinical use in recent surveys because they are not uniformly elevated in men with advanced prostate cancer. Due to the limitations of currently available biomarkers, the identification and characterization of prostate specific genes is essential to the development of more accurate diagnostic methods and therapeutic targets. In many cases, the clinical potential of novel tumor markers can be optimized by utilizing them in combination with other tumor markers in the development of diagnostic and treatment modalities.

Normal prostate tissue consists of three distinct non-stromal cell populations, luminal secretory cells, basal cells, and endocrine paracrine cells. Phenotypic similarities between normal luminal cells and prostate cancer cells, including the expression of PSA, have suggested that prostate adenocarcinomas derive from luminal cells. However, a number of recent studies suggest that at least some prostate cancers can arise from the transformation of basal cells and report the expression of various genes in normal prostate basal cells as well as in prostate carcinoma cells. These genes include prostate stem cell antigen (PSCA), c-met and Bcl-2. Because none of these genes is universally expressed in all basal cells and prostate carcinomas, the utility of these genes as diagnostic markers is limited. Likewise, because PSA is expressed in luminal secretory cells in normal prostate tissue, this antigen has limited utility as a marker for basal cell derived carcinomas.

Thus, there exists a need for the identification of additional prostate specific genes that can be used as diagnostic markers and therapeutic targets for prostate cancer. The present invention satisfies this need and provides related advantages as well.

SUMMARY OF THE INVENTION

The present invention provides a PAMP nucleic acid molecule containing a nucleic acid sequence encoding substantially a PAMP polypeptide. A PAMP nucleic acid molecule of the invention encodes substantially the amino acid sequence shown as SEQ ID NO:2. A PAMP nucleic acid molecule can encode, for example, the amino acid sequence shown as SEQ ID NO:2 and, in one embodiment, contains the nucleotide sequence shown as SEQ ID NO:1.

Further provided by the invention is a substantially pure PAMP nucleic acid probe which contains substantially the nucleotide sequence of nucleotides 1 to 3221 of SEQ ID NO:1, or a fragment thereof, provided that the probe does not have the nucleotide sequence of AA363808, AW959484, BE165930, nucleotides 1 to 614 of BE893201 or nucleotides 1 to 1530 of AK026780.

The invention also provides a substantially pure PAMP nucleic acid probe which contains at least 10 contiguous nucleotides of SEQ ID NO:1, where the contiguous nucleotides include at least one nucleotide of the nucleotide sequence shown as position 1 to position 3221 of SEQ ID NO:1, provided that the probe does not have the nucleotide sequence of AA363808, AW959484, BE165930, nucleotides 1 to 614 of BE893201 or nucleotides 1 to 1530 of AK026780. Such a PAMP nucleic acid probe can contain, for example, at least 15 contiguous nucleotides of SEQ ID NO:1, and can be, for example, 15 to 18 nucleotides in length. If desired, a substantially pure PAMP nucleic acid probe of the invention can further include a detectable label.

The invention also provides a substantially pure PAMP polypeptide which contains substantially the amino acid sequence shown as SEQ ID NO:2. In one embodiment, a substantially pure PAMP polypeptide of the invention has the amino acid sequence SEQ ID NO:2.

In addition, the invention provides a substantially pure PAMP polypeptide fragment, which includes at least eight contiguous amino acids of residues 1 to 1074 of SEQ ID NO:2. Such a PAMP polypeptide fragment can include, for example, at least ten contiguous amino acids of residues 1 to 1074 of SEQ ID NO:2.

The present invention provides a method of diagnosing or predicting susceptibility to a prostate neoplastic condition in an individual. The method is practiced by obtaining a sample from the individual;

measuring a test expression level of PAMP RNA by hybridization with a PAMP nucleic acid probe comprising at least 10 contiguous nucleotides of SEQ ID NO:1, the contiguous nucleotides including at least one nucleotide of the nucleotide sequence shown as position 1 to position 3221 of SEQ ID NO:1 in the sample; and comparing the test expression level of PAMP RNA to a control expression level of PAMP RNA, where a test expression level 2-fold or more greater than the control expression level indicates the presence of a prostate neoplastic condition. In a method of the invention, the sample can contain a prostate cell or a prostate tissue, and the control expression level can be determined using a normal prostate cell or an androgen-dependent cell line. The sample can be, for example, a fluid such as blood, serum, urine or semen. In one embodiment, the PAMP nucleic acid probe contains at least 10 contiguous nucleotides of SEQ ID NO:1, the contiguous nucleotides including at least one nucleotide of the nucleotide sequence shown as position 1 to position 3221 of SEQ ID NO:1, provided the probe does not have the nucleotide sequence of AA363808, AW959484, BE165930, nucleotides 1 to 614 of BE893201 or nucleotides 1 to 1530 of AK026780. A PAMP nucleic acid probe useful in a method of the invention can be, for example, 15 to 18 nucleotides in length and can contain, if desired, a detectable label.

The invention also provides a method of diagnosing or predicting susceptibility to a prostate neoplastic condition in an individual by obtaining a sample from the individual; measuring a test expression level of PAMP polypeptide by contacting a cell, a cell lysate, or fractionated sample thereof, from the individual with a binding agent selective for PAMP polypeptide residues 1 to 1074 of SEQ ID NO:2, and determining the amount of selective binding of the agent; and comparing the test expression level of PAMP polypeptide to a control expression level of PAMP polypeptide, where a test expression level 2-fold or more greater than the control expression level indicates the presence of a prostate neoplastic condition. In a method of the invention, the binding agent selective for the PAMP polypeptide residues 1 to 1074 of SEQ ID NO:2 can include, for example, an antibody, and can further include, if desired, a detectable label.

Further provided by the invention is a method of diagnosing metastatic prostate cancer in an individual by obtaining a sample from the individual, wherein the sample is not a prostate sample; measuring a test expression level of PAMP RNA by hybridization with a PAMP nucleic acid probe comprising at least 10 contiguous nucleotides of SEQ ID NO:1, the contiguous nucleotides including at least one nucleotide of the nucleotide sequence shown as position 1 to position 3221 of SEQ ID NO:1 in the sample; and comparing the test expression level of PAMP RNA to a control expression level of PAMP RNA, where a significant test expression level as compared to the control expression level indicates the presence of metastatic prostate cancer.

In addition, the invention provides a method of diagnosing metastatic prostate cancer in an individual by obtaining a sample from the individual, where the sample is not a prostate sample; measuring a test expression level of PAMP polypeptide by contacting a cell, a cell lysate, or fractionated sample thereof, from the individual with a binding agent selective for PAMP polypeptide residues 1 to 1074 of SEQ ID NO:2, and determining the amount of selective binding of the agent; and comparing the test expression level of PAMP polypeptide to a control expression level of PAMP polypeptide, where a significant test expression level as compared to the control expression level indicates the presence of metastatic prostate cancer.

BRIEF DESCRIPTION OF THE DRAWINGS

FIG. 1 shows the full-length nucleotide (SEQ ID NO: 1) and amino acid (SEQ ID NO: 2) sequence of PAMP. Predicted transmembrane domains are underlined.

FIG. 5 shows RNA in situ hybridization with PAMP sense and antisense probes. A: Anti-sense probe of PAMP hybridized to a section of prostate cancer tissue sample. B: Sense probe of PAMP hybridized to prostate cancer section. C: Anti-sense probe of PAMP hybridized to normal prostate gland section. D: Sense probe of PAMP hybridized to normal prostate gland section.

DETAILED DESCRIPTION OF THE INVENTION

Figure 2A:
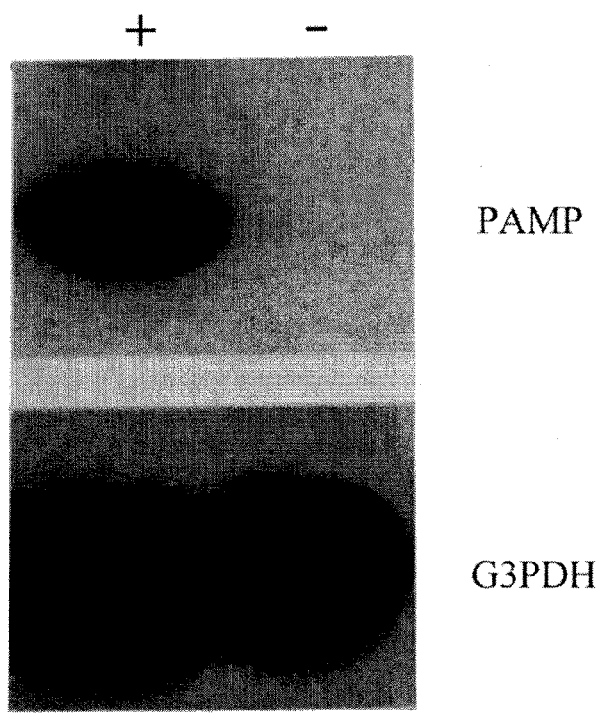
FIG. 2 shows northern analysis of PAMP expression in androgen-stimulated cells. Left panel: "+" indicates androgen-stimulated RNA; "−" indicates androgen-starved RNA. Right panel: A time course northern blot showing PAMP expression at 4, 8, 12, 16, 24, 36, 48 hours after androgen stimulation.

This invention is directed to the discovery of the full-length coding sequence for PAMP, a gene with several transcripts expressed specifically in the prostate. The prostate-specific nucleic acid sequence and encoded gene product are useful as both diagnostic markers for neoplastic conditions of the prostate and as targets for therapy.

As disclosed herein in Example I, the PAMP cDNA contains 4485 nucleotides and is predicted to encode a protein of 1382 amino acids with at least 4 transmembrane domains (see FIG. 1). As further disclosed herein, PAMP expression is induced by androgen in the prostate carcinoma cell line LNCaP. Expression of the PAMP transcript was induced by 4 hours and maintained at least to 48 hours following androgen treatment (see FIG. 2). As further disclosed herein, expression of the 2.0 and 3.2 kb PAMP transcripts was specific to prostate among 16 adult human tissues assayed by northern analysis (FIG. 3), while the 5.0 and 6.5 kb forms were expressed in prostate, ovary and testis. Furthermore, among 50 human fetal and adult tissues assayed, significant expression was only detected in the prostate (see FIG. 4). As further disclosed herein in Example III, RNA in situ analysis demonstrated that PAMP was expressed in epithelial cells in normal prostate and prostate cancer cells. These results demonstrate that PAMP is an androgen-regulated prostate-specific gene product.

Based on these results, the invention provides methods for diagnosing prostate neoplastic conditions. As discussed above, a PAMP gene of the invention is primarily expressed in prostate cells and becomes elevated in response to androgens. As such, a PAMP nucleic acid molecule or polypeptide of the invention can be used alone or in combination with other molecules as a specific marker for prostate cells and prostate neoplastic conditions.

PAMP Nucleic Acid Molecules

The present invention provides a PAMP nucleic acid molecule containing a nucleic acid sequence encoding substantially the amino acid sequence shown as SEQ ID NO:2. A PAMP nucleic acid molecule can encode, for example, the amino acid sequence shown as SEQ ID NO:2 and, in one embodiment, contains the nucleotide sequence shown as SEQ ID NO:1.

The nucleic acid sequence of the PAMP cDNA (SEQ ID NO:1) and the deduced amino acid sequence (SEQ ID NO: 2) were determined as disclosed in Example I. As shown in FIG. 1, the PAMP cDNA contains 4485 nucleotides and is predicted to encode a protein of 1382 amino acids.

The nucleic acid molecules of the invention and short oligonucleotide probes corresponding to unique sequences are useful in a variety of diagnostic procedures which employ probe hybridization methods. One advantage of employing nucleic acid hybridization in diagnostic procedures is that very small amounts of sample can be used because the analyte nucleic acid molecule can be amplified to many copies by, for example, polymerase chain reaction (PCR) or other well known methods for nucleic acid molecule amplification and synthesis.

As used herein, the term "nucleic acid molecule" is intended to mean a single- or double-stranded DNA or RNA molecule including, for example, genomic DNA, cDNA and mRNA. The term is intended to include nucleic acid molecules of both synthetic and natural origin. A nucleic acid molecule of natural origin can be derived from any animal, such as a human, non-human primate, mouse, rat, rabbit, bovine, porcine, ovine, canine, feline, or amphibian, or from a lower eukaryote. A nucleic acid molecule of the invention can be of linear, circular or branched configuration, and can represent either the sense or antisense strand, or both, of a native nucleic acid molecule. A nucleic acid molecule of the invention can further incorporate a detectable moiety such as a radiolabel, a fluorochrome, a ferromagnetic substance, a luminescent tag or a detectable binding agent such as biotin.

As used herein, the term "substantially pure nucleic acid molecule" is intended to mean a nucleic acid molecule that is substantially free from cellular components or other contaminants that are not the desired molecule. A substantially pure nucleic acid molecule can also be sufficiently homogeneous so as to resolve as a band by gel electrophoresis, and generate a nucleotide sequence profile consistent with a predominant species.

Nucleic Acid Probes

A nucleic acid probe of the invention can contain substantially the nucleotide sequence of a portion of nucleotides 1 to 3221 of SEQ ID NO:1. The term "probe," as used herein in reference to a substantially pure nucleic acid molecule of the invention, is intended to refer to a portion of the nucleic acid molecule having the ability to selectively hybridize with the parent nucleic acid molecule. The term "selectively hybridize" refers to an ability to bind the parent nucleic acid molecule without substantial cross-reactivity with a molecule that is not the parent nucleic acid molecule. Therefore, the term includes specific hybridization where there is little or no detectable cross-reactivity with other nucleic acid molecules. The term also includes minor cross-reactivity with other molecules provided hybridization to the subject nucleic acid molecule is distinguishable from hybridization to the cross-reactive species. Thus, a probe of the invention can be used, for example, as a PCR primer to selectively amplify a nucleic acid molecule of the invention; as a selective primer for 5' or 3' RACE to determine additional 5' or 3' sequence of a nucleic acid molecule of the invention; as a selective probe to identify or isolate a nucleic acid molecule of the invention on a RNA or DNA blot, or genomic or cDNA library; or as a selective inhibitor of transcription or translation of PAMP in a tissue, cell or cell extract. In one embodiment, the following sequences are excluded as nucleic acid probes of the invention: one or any combination of AA363808, AW959484, BE165930, nucleotides 1 to 614 of BE893201 or nucleotides 1 to 1530 of AK026780. In another embodiment, one or any combination of AA363808, AW959484, BE165930, nucleotides 1 to 614 of BE893201, nucleotides 1 to 1530 of AK026780, or nucleotides 1531 to 2000 of AK026780 is excluded from a probe of the invention. In a further embodiment, one or any combination of AA363808, AW959484, BE165930, BE893201, or AK026780, or a subsequence thereof containing at least ten contiguous nucleotides of any of these five sequences, is excluded from a probe of the invention.

Thus, the invention provides a substantially pure PAMP nucleic acid probe which contains substantially the nucleotide sequence of nucleotides 1 to 3221 of SEQ ID NO:1, or a fragment thereof, provided that the probe does not have the nucleotide sequence of AA363808, AW959484, BE165930, nucleotides 1 to 614 of BE893201 or nucleotides 1 to 1530 of AK026780.

In one embodiment, the invention provides a substantially pure PAMP nucleic acid probe which contains at least 10 contiguous nucleotides of SEQ ID NO:1, where the contiguous nucleotides include at least one nucleotide of the nucleotide sequence shown as position 1 to position 3221 of SEQ ID NO:1, provided that the probe does not have the nucleotide sequence of AA363808, AW959484, BE165930, nucleotides 1 to 614 of BE893201 or nucleotides 1 to 1530 of AK026780. Such a PAMP nucleic acid probe can contain, for example, at least 15 contiguous nucleotides of SEQ ID NO:1, and can be, for example, 15 to 18 nucleotides in length. If desired, a substantially pure PAMP nucleic acid probe of the invention can further include a detectable label.

As used herein, the term "probe" refers to a portion of a subject nucleic acid molecule having at least 10 nucleotides. A probe of the invention includes at least 10 contiguous nucleotides corresponding to the reference nucleic acid molecule, and can include at least 11, 12, 13, 14, 15, 16, 17, 18, 19, 20 or at least 25 nucleotides and, if desired, can include at least 30, 40, 50, 100, 300 or 500 nucleotides, and can include up to the full length of the reference nucleic acid molecule minus one nucleotide. Probes of such lengths are able to selectively hybridize with the subject nucleic acid molecule in a variety of detection formats described herein.

As used herein, the term "substantially the nucleotide sequence" in reference to a nucleic acid molecule or nucleic acid probe of the invention includes sequences having one or more additions, deletions or substitutions with respect to the reference sequence, so long as the nucleic acid molecule retains its ability to selectively hybridize with the subject nucleic acid molecule.

Nucleic acid molecules and probes of the invention are useful as hybridization probes in diagnostic procedures. The probes can be as long as the full length transcript or as short as about 10-15 nucleotides, and preferably about 15-18 nucleotides. A probe of the invention can correspond to coding region or untranslated region sequence. The particular application and degree of desired specificity will be one consideration well known to those skilled in the art in selecting a probe. For example, if it is desired to detect PAMP and other related species, the probe can correspond to a coding sequence and be used in low stringency hybridization conditions. Alternatively, using high stringency conditions with a probe of the invention will select a PAMP nucleic acid molecule having substantially the nucleotide sequence shown as SEQ ID NO: 1. Untranslated region sequences corresponding to a PAMP transcript can also be used to construct probes since there is little evolutionary pressure to conserve non-coding domains. Probes as small as 15 nucleotides are statistically unique sequences within the human genome. Therefore, fragments of the PAMP sequences of 15 nucleotides or more in length can be constructed from essentially any region of a PAMP cDNA, mRNA or promoter/regulatory region and be capable of uniquely hybridizing to PAMP DNA or RNA.

Nucleic acid probes can be produced recombinantly or chemically synthesized using methods well known in the art. Additionally, PAMP hybridization probes can be labeled with a variety of detectable labels including, for example, radio-isotopes, fluorescent tags, reporter enzymes, biotin and other ligands. Such detectable labels can additionally be coupled with, for example, colorimetric or photometric indicator substrate for spectrophotometric detection. Methods for labeling and detecting such probes are well known in the art and can be found described in, for example, Sambrook et al., *Molecular Cloning: A Laboratory Manual*, 2nd ed., Cold Spring Harbor Press, Plainview, N.Y. (1989), and Ausubel et al., *Current Protocols in Molecular Biology* (Supplement 47), John Wiley & Sons, New York (1999).

The nucleic acid probes of the invention can be hybridized under various stringency conditions readily determined by one skilled in the art. Depending on the particular assay, one skilled in the art can readily vary the stringency conditions to optimize detection of a PAMP nucleic acid molecule.

In general, the stability of a hybrid is a function of the ion concentration and temperature. Typically, a hybridization reaction is performed under conditions of lower stringency, followed by washes of varying, but higher, stringency. Moderately stringent hybridization refers to conditions that permit a nucleic acid molecule such as a probe to bind a complementary nucleic acid molecule. The hybridized nucleic acid molecules generally have at least 60% identity, at least 75% identity, at least 85% identity; or at least 90% identity. Moderately stringent conditions are conditions equivalent to hybridization in 50% formamide, 5× Denhart's solution, 5× SSPE, 0.2% SDS at 42° C., followed by washing in 0.2× SSPE, 0.2% SDS, at 42° C. High stringency conditions can be provided, for example, by hybridization in 50% formamide, 5× Denhart's solution, 5×SSPE, 0.2% SDS at 42°C., followed by washing in 0.1×SSPE, and 0.1% SDS at 65° C.

The phrase "low stringency hybridization" refers to conditions equivalent to hybridization in 10% formamide, 5× Denhart's solution, 6×SSPE, 0.2% SDS at 22° C., followed by washing in 1×SSPE, 0.2% SDS, at 37° C. Denhart's solution contains 1% Ficoll, 1% polyvinylpyrolidone, and 1% bovine serum albumin (BSA). 20×SSPE (sodium chloride, sodium phosphate, ethylene diamide tetraacetic acid (EDTA)) contains 3M sodium chloride, 0.2M sodium phosphate, and 0.025 M (EDTA). Other suitable moderate stringency and high stringency hybridization buffers and conditions are well known to those of skill in the art and are described, for example, in Sambrook et al., *Molecular Cloning: A Laboratory Manual*, 2nd ed., Cold Spring Harbor Press, Plainview, N.Y. (1989); and Ausubel et al., supra, 1999). Nucleic acid molecules encoding polypeptides hybridize under moderately stringent or high stringency conditions to substantially the entire sequence, or substantial portions, for example, typically at least 15-30 nucleotides of the nucleic acid sequence set forth in SEQ ID NO:1.

The invention also provides a modification of a PAMP nucleotide sequence that hybridizes to a PAMP nucleic acid molecule, for example, a nucleic acid molecule referenced as SEQ ID NO:1, under moderately stringent conditions. Modifications of PAMP nucleotide sequences, where the modification has at least 60% identity to a PAMP nucleotide sequence, are also provided. The invention also provides modification of a PAMP nucleotide sequence having at least 65% identity, at least 70% identity, at least 75% identity, at least 80% identity, at least 85% identity, at least 90% identity, or at least 95% identity.

Identity of any two nucleic acid sequences can be determined by those skilled in the art based, for example, on a BLAST 2.0 computer alignment, using default parameters. BLAST 2.0 searching is available at http://www.ncbi.nlm.nih.gov/gorf/b12.html., as described by Tatiana et al., *FEMS Microbiol Lett.* 174:247-250 (1999); Altschul et al., *Nucleic Acids Res.*, 25:3389-3402 (1997).

PAMP Polypeptides

The invention also provides a substantially pure PAMP polypeptide which contains substantially the amino acid sequence shown as SEQ ID NO:2. In one embodiment, a substantially pure PAMP polypeptide of the invention has the amino acid sequence SEQ ID NO:2.

In addition, the invention provides a substantially pure PAMP polypeptide fragment, which includes at least eight contiguous amino acids of residues 1 to 1074 of SEQ ID NO:2. Such a PAMP polypeptide fragment can include, for example, at least ten contiguous amino acids of residues 1 to 1074 of SEQ ID NO:2.

In one embodiment, the invention provides a PAMP polypeptide fragment that includes at least eight contiguous amino acids of residues 1 to 1074 of SEQ ID NO:2, provided that the fragment does not contain eight or more contiguous amino acids of AK026780. In a further embodiment, the invention provides a PAMP polypeptide fragment that includes at least eight contiguous amino acids of residues 1 to 1074 of SEQ ID NO:2, provided that the fragment does not contain eight or more contiguous amino acids of AK026780, or eight or more contiguous amino acids encoded by any of the six reading frames of AA363808, AW959484, BE165930, BE893201 or AK026780.

Polypeptide fragments of the invention include peptides that can function as antigenic determinants to generate antibodies that are selective for a PAMP polypeptide encoded by substantially residues 1 to 1074 of SEQ ID NO:2.

Exemplary polypeptide fragments include those fragments having amino acids 1 to 8, 2 to 9, 3 to 10, etc. Other polypeptide fragments of residues 1 to 1074 shown in FIG. 1 are also included as peptides that are potential antigenic fragments capable of eliciting an immune response to generate antibodies selective for PAMP polypeptide residues 1 to 1074. It is understood that, while eight residues is the minimum length of a polypeptide fragment of the invention, a fragment can be longer and can include 9, 10, 11, 12, 13, 14, 15, 18, 20, 25, 30, 35, 40, 45 or more contiguous amino acids of residues 1 to 1074 of the PAMP polypeptide shown as SEQ ID NO:2.

The nucleic acid molecules and polypeptides of the invention encode a PAMP polypeptide. The term "PAMP polypeptide" as used herein, means a polypeptide that is structurally similar to human PAMP and that at least one biological activity of PAMP. Such a PAMP polypeptide has 50% or more sequence identity to SEQ ID NO:2, and can have 55%, 60%, 65%, 70%, 75%, 80%, 85%, 90%, 95% or more sequence identity to human PAMP (SEQ ID NO:2). Percent amino acid identity can be determined using Clustal W version 1.7 (Thompson et al., *Nucleic Acids Res.* 22:4673-4680 (1994))).

The present invention is directed to the full-length PAMP polypeptide sequence or large fragments of this full-length sequence. Thus, the term "PAMP polypeptide," as used herein, refers to a polypeptide corresponding to at least 350 of the 1382 residues of human PAMP. In view of the above, it is understood that a fragment containing, for example, residues 1075 to 1382 of SEQ ID NO:2 is not a "PAMP polypeptide" as defined herein.

Thus, it is clear to the skilled person that the term "PAMP polypeptide" encompasses polypeptides with one or more naturally occurring or non-naturally occurring amino acid substitutions, deletions or insertions as compared to SEQ ID NO: 2, provided that the peptide has at least 50% amino acid identity with SEQ ID NO: 2 and corresponds to at least 350 residues of full-length PAMP. A PAMP polypeptide can be, for example, a naturally occurring variant of human PAMP (SEQ ID NO: 2), a species homolog including mammalian and non-mammalian homologs and murine, bovine, and primate homologs, a PAMP mutated by recombinant techniques, and the like. In view of the above, it is clear to the skilled person that the Drosophila polypeptide encoded by AAF57545.1 (CG11237) and the C. elegans polypeptide encoded by ZK520 (T27880), which each share 44% amino acid identity with human PAMP (SEQ ID NO:2) are not encompassed by the invention.

Modifications to SEQ ID NO: 2 that are encompassed within the invention include, for example, an addition, deletion, or substitution of one or more conservative or non-conservative amino acid residues; substitution of a compound that mimics amino acid structure or function; or addition of chemical moieties such as amino or acetyl groups.

In one embodiment, the invention provides a PAMP polypeptide having an amino acid sequence corresponding to at least 350 of the 1382 residues of human PAMP, provided that the polypeptide does not contain the sequence of AK026780. In another embodiment, the invention provides a PAMP polypeptides having an amino acid sequence corresponding to at least 350 of the 1382 residues of human PAMP, provided that the polypeptide does not contain the sequence of AK026780 or the amino acid sequence encoded by any of the six reading frames of AA363808, AW959484, BE165930, BE893201 or AK026780.

The invention also provides antibodies that specifically bind a PAMP polypeptide. In one embodiment, the invention provides an antibody selective for PAMP polypeptide residues 1 to 1074, or a PAMP polypeptide fragment containing at least eight contiguous amino acids of residues 1 to 1074 of SEQ ID NO:2.

As used herein, the term "antibody" is used in its broadest sense to include polyclonal and monoclonal antibodies, as well as antigen binding fragments of such antibodies. With regard to an antibody of the invention which is selective for PAMP polypeptide residues 1 to 1074 or a polypeptide fragment thereof, the term "antigen" means a native or synthesized fragment of PAMP residues 1 to 1074. Such an antibody of the invention, or antigen binding fragment of such an antibody, is characterized by having specific binding activity for PAMP polypeptide residues 1 to 1074, or a PAMP polypeptide fragment, of at least about $1 \times 10^5$ $M^{-1}$. Thus, Fab, $F(ab')_2$, Fd and Fv fragments of an anti-PAMP antibody, which retain specific binding activity for PAMP polypeptide residues 1 to 1074, or a polypeptide fragment thereof, are included within the definition of an antibody. Specific binding activity can be readily determined by one skilled in the art, for example, by comparing the binding activity of the antibody to PAMP polypeptide residues 1 to 1074 or a polypeptide fragment thereof versus a control polypeptide that does not include PAMP polypeptide residues 1 to 1074. Methods of preparing polyclonal or monoclonal antibodies are well known to those skilled in the art (see, for example, Harlow and Lane, Antibodies: A Laboratory Manual, Cold Spring Harbor Laboratory Press (1988)).

In addition, the term "antibody" as used herein includes naturally occurring antibodies as well as non-naturally occurring antibodies, including, for example, single chain antibodies, chimeric, bifunctional and humanized antibodies, as well as antigen-binding fragments thereof. Such non-naturally occurring antibodies can be constructed using solid phase peptide synthesis, can be produced recombinantly or can be obtained, for example, by screening combinatorial libraries consisting of variable heavy chains and variable light chains as described by Huse et al. (Science 246:1275-1281 (1989)). These and other methods of making, for example, chimeric, humanized, CDR-grafted, single chain, and bifunctional antibodies are well known to those skilled in the art (Winter and Harris, Immunol. Today 14:243-246 (1993); Ward et al., Nature 341:544-546 (1989); Harlow and Lane, supra, 1988); Hilyard et al., Protein Engineering: A practical approach (IRL Press 1992); Borrabeck, Antibody Engineering, 2d ed. (Oxford University Press 1995)).

An antibody of the invention can be prepared using as an immunogen a PAMP polypeptide, which can be prepared from natural sources or produced recombinantly, or a PAMP polypeptide fragment of the invention, which contains at least 8 contiguous amino acids of residues 1 to 1074 of SEQ ID NO:2. Such polypeptide fragments are functional antigenic fragments if the antigenic peptides can be used to generate an antibody selective for PAMP polypeptide residues 1 to 1074 of SEQ ID NO:2. As is well known in the art, a non-immunogenic or weakly immunogenic PAMP polypeptide or polypeptide fragment can be made immunogenic by coupling the hapten to a carrier molecule such as bovine serum albumin (BSA) or keyhole limpet hemocyanin (KLH). Various other carrier molecules and methods for coupling a hapten to a carrier molecule are well known in the art (see, for example, Harlow and Lane, supra, 1988). An immunogenic PAMP polypeptide fragment can also be generated by expressing the peptide portion as a fusion protein, for example, to glutathione S transferase (GST), polyHis or the like. Methods for expressing peptide fusions are well known to those skilled in the art (Ausubel et al., Current Protocols in Molecular Biology (Supplement 47), John Wiley & Sons, New York (1999)).

Diagnostic Methods

Methods of diagnosing or predicting susceptibility to a prostate neoplastic condition in an individual further are provided by the invention. The methods of the invention are practiced by obtaining a sample from an individual; measuring a test expression level of PAMP in the sample; and comparing the test expression level of PAMP to a control expression level of PAMP, where a test expression level 2-fold or more greater than the control expression level indicates the presence of a prostate neoplastic condition. In a method of the invention, the sample can contain, for example, a prostate cell or prostate tissue and, in one embodiment, is a fluid such as blood, serum, urine or semen. The control expression level can be determined, for example, using a normal prostate cell or an androgen-dependent cell line.

In a diagnostic method of the invention, a test expression level can be determined, for example, by measuring the amount of PAMP RNA and, in one embodiment, the amount of PAMP RNA is determined by hybridization with a PAMP nucleic acid probe containing at least 10 contiguous nucleotides of SEQ ID NO:1 and also including at least one nucleotide of the nucleotide sequence shown as position 1 to position 3221 of SEQ ID NO:1, provided that the probe does not have the nucleotide sequence of AA363808, AW959484, BE165930, nucleotides 1 to 614 of BE893201 or nucleotides 1 to 1530 of AK026780. A nucleic acid probe useful in a method of the invention can be, for example, 15 to 18 nucleotides in length, and, if desired, can further include a detectable label.

In a diagnostic method of the invention, a test expression level also can be determined, for example, by measuring the amount of PAMP polypeptide. In one embodiment, a diagnostic method of the invention is practiced by determining an amount of PAMP polypeptide by contacting a cell, a cell lysate, or fractionated sample thereof from the individual to be diagnosed with a binding agent selective for PAMP polypeptide residues 1 to 1074 of SEQ ID NO:2, and determining the amount of selective binding of the agent. A binding agent selective for PAMP polypeptide residues 1 to 1074 of SEQ ID NO:2 can be, for example, an antibody, and, if desired, can further include a detectable label.

Figure 4:
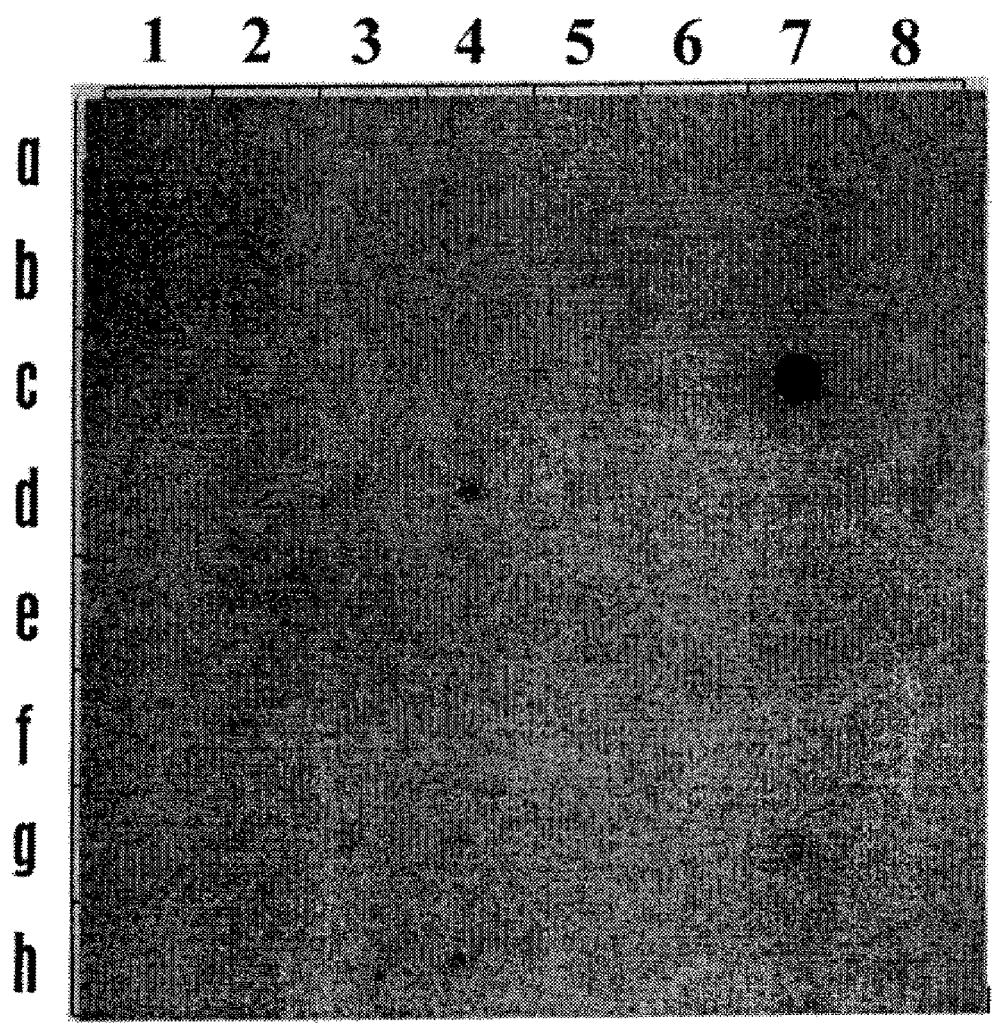
FIG. 4 shows hybridization of PAMP to a multiple tissue expression (MTE) array (ClonTech) containing 50 human tissues. The RNAs are as follows: A1, whole brain; A2, amygdala; A3, caudate nucleus; A4, cerebellum; A5, cerebral cortex; A6, frontal lobe; A7, hippocampus; A8, medulla oblongata; B1, occipital lobe; B2, putamen; B3; substantia nigra; B4, temporal lobe; B5, thalamus; B6, acumens; B7, spinal cord; C1, heart; C2, aorta; C3, skeletal muscle; C4, colon; C5, bladder; C6, uterus; C7, prostate; C8, stomach; D1, testis; D2, ovary; D3, pancreas; D4, pituitary gland; D5, adrenal gland; D6, thyroid gland; D7, salivary gland; D8, mammary gland; E1, kidney; E2, liver; E3, small intestine; E4, spleen; E5, thymus; E6, peripheral leukocyte; E7, lymph node; E8, bone marrow; F1, appendix; F2, lung; F3, trachea; F4, placenta; G1, fetal brain; G2, fetal heart; G3, fetal kidney; G4, fetal liver; G5, fetal spleen; G6, fetal thymus; G7, fetal lung; H1, yeast total RNA; H2, yeast tRNA; H3, $E.\ Coli$ rRNA; H4, $E.\ Coli$ DNA; H5, poly r(A); H6, human $C_0t$ 1 DNA; H7, human DNA; H8, human DNA; B8, F5-F8, G8 contain no RNAs.

As disclosed herein in FIG. 4, PAMP was most highly expressed in prostate among 50 human tissues analyzed. These results indicate that PAMP expression outside of the prostate can be indicative of advanced prostate cancer, in which cancerous prostate cells have metastasized. Thus, the invention also provides a method of diagnosing metastatic prostate cancer in an individual by obtaining a sample from the individual, where the sample is not a prostate sample; measuring a test expression level of PAMP in the sample; and comparing the test expression level of PAMP to a control expression level of PAMP, where a significant test expression level as compared to the control expression level indicates the presence of metastatic prostate cancer.

As described herein, the term "prostate neoplastic condition" is intended to refer to a benign or malignant and metastatic prostate lesion of proliferating cells. For example, primary prostate tumors are classified into stages TX, T0, T1, T2, T3, and T4. Metastatic prostate cancer is classified into stages D1, D2, and D3. The term is also intended to include prostate neoplasm.

As used herein, the term "sample" is intended to mean any biological fluid, cell, tissue, organ or portion thereof, that includes or potentially includes nucleic acid molecules and polypeptides of the invention. The term includes samples present in an individual as well as samples obtained or derived from the individual. For example, a sample can be a histologic section of a specimen obtained by biopsy, or cells that are placed in or adapted to tissue culture. A sample further can be a subcellular fraction or extract, or a crude or substantially pure nucleic acid molecule or protein preparation. A sample can be prepared by methods known in the art suitable for the particular format of the detection method.

As used herein, the term "detectable label" refers to a molecule that renders a nucleic acid molecule of the invention detectable by an analytical method. An appropriate detectable label depends on the particular assay format; such labels are well known by those skilled in the art. For example, a detectable label selective for a nucleic acid molecule can be a complementary nucleic acid molecule, such as a hybridization probe, that selectively hybridizes to the nucleic acid molecule. A hybridization probe can be labeled with a measurable moiety, such as a radioisotope, fluorochrome, chemiluminescent marker, biotin, or other moiety known in the art that is measurable by analytical methods. A detectable label also can be a nucleic acid molecule without a measurable moiety. For example, PCR or RT-PCR primers can be used without conjugation to selectively amplify all or a desired portion of the nucleic acid molecule. The amplified nucleic acid molecules can then be detected by methods known in the art.

As used herein, the term "binding agent" when used in reference to a PAMP polypeptide, is intended to mean a compound, including a simple or complex organic molecule, a metal containing compound, carbohydrate, peptide, protein, peptidomimetic, glycoprotein, lipoprotein, lipid, nucleic acid molecule, antibody, or the like that selectively binds a PAMP polypeptide or PAMP polypeptide fragment, or to a PAMP gene regulatory sequence such as a promoter or enhancer element. For example, a binding agent can be a polypeptide that selectively binds with high affinity or avidity to a PAMP polypeptide, without substantial cross-reactivity with other polypeptides that are unrelated to a PAMP polypeptide. The affinity of a binding agent that selectively binds a PAMP polypeptide will generally be greater than about $10^5$ $M^{-1}$ and more preferably greater than about $10^6$ $M^{-1}$. High affinity interactions can be preferred, and will generally be greater than about $10^8$ $M^{-1}$ to $10^9$ $M^{-1}$. Specific examples of such selective binding agents include a polyclonal or monoclonal antibody selective for a PAMP polypeptide or peptide fragment thereof, nucleic acid molecule, nucleic acid analog, or small organic molecule, identified, for example, by affinity screening of a library. For certain applications, a binding agent can be utilized that preferentially recognizes a particular conformational or post-translationally modified state of a PAMP polypeptide. The binding agent can be labeled with a detectable moiety, if desired, or rendered detectable by specific binding to a detectable secondary binding agent.

As used herein, the term "test expression level" is used in reference to a PAMP mRNA or polypeptide expression and refers to the extent, amount or rate of synthesis of the nucleic acid sequence shown as SEQ ID NO: 1 or the PAMP polypeptide shown as SEQ ID NO: 2. The amount or rate of synthesis can be determined by measuring the accumulation or synthesis of PAMP RNA, PAMP polypeptide or by measuring an activity associated with a PAMP polypeptide.

In methods of the invention, the sample can be, for example, a prostate cell or prostate tissue such as a tissue biopsy. A sample can also be a fluid sample, for example, blood, serum, urine or semen. A normal sample can be, for example, a normal prostate cell or an androgen-dependent cell line.

In methods of the invention, a test expression level can be determined by measuring the amount of PAMP RNA, for example, by hybridization with a nucleic acid probe comprising substantially the nucleotide sequence of SEQ ID NO:1, or a fragment thereof. The probe can be, for example, an oligonucleotide of 15 to 18 nucleotides in length and, if desired, can contain a detectable label.

In one embodiment, a test expression level is determined by measuring the amount of PAMP RNA by hybridization with a PAMP nucleic acid probe that contains at least 10 contiguous nucleotides of SEQ ID NO:1, where the contiguous nucleotides include at least one nucleotide of the nucleotide sequence shown as position 1 to position 3221 of SEQ ID NO:1, provided that the probe does not have the nucleotide sequence of AA363808, AW959484, BE165930, nucleotides 1 to 614 of BE893201 or nucleotides 1 to 1530 of AK026780.

Alternatively, a test expression level can be determined by measuring the amount of PAMP polypeptide. The amount of PAMP polypeptide can be determined, for example, by contacting a cell, a cell lysate or fractionated sample thereof, from an individual with a binding agent selective for a PAMP polypeptide and determining the amount of selective binding of the agent. The selective binding agent can be, for example, an antibody or other molecule identified as a PAMP polypeptide binding agent by the methods disclosed herein and, if desired, can contain a detectable label.

In one embodiment, a test expression is determined by measuring the amount of PAMP polypeptide using a binding agent selective for PAMP polypeptide residues 1 to 1074 of SEQ ID NO:2.

A prostate neoplastic condition is a benign or malignant prostate lesion of proliferating cells. Prostate neoplastic conditions include, for example, prostate interepithelial neoplasia (PIN) and prostate cancer. Prostate cancer is an uncontrolled proliferation of prostate cells which can invade and destroy adjacent tissues as well as metastasize. Primary prostate tumors can be classified into stages TX, T0, T1, T2, T3, and T4 and metastatic tumors can be classified into stages D1, D2 and D3. Similarly, there are classifications known by those skilled in the art for the progressive stages of precancerous lesions or PIN. The methods herein are applicable for the diagnosis or treatment of any or all stages of prostate neoplastic conditions.

The methods of the invention are also applicable to prostate pathologies other than neoplastic conditions. Such other pathologies include, for example, benign prostatic hyperplasia (BPH) and prostatitis. BPH is one of the most common diseases in adult males. Histological evidence of BPH has been found in more than 40% of men in their fifties and almost 90% of men in their eighties. The disease results from the accumulation of non-malignant nodules arising in a small region around the proximal segment of the prostatic urethra which leads to an increase in prostate volume. If left untreated, BPH can result in acute and chronic retention of urine, renal failure secondary to obstructive uropathy, serious urinary tract infection and irreversible bladder decompensation. Prostatitis is an infection of the prostate. Other prostate pathologies known to those skilled in the art exist as well and are similarly applicable for diagnosis or treatment using the methods of the invention. Various neoplastic conditions of the prostate as well as prostate pathologies can be found described in, for example, *Campbell's Urology*, Seventh Edition, W.B. Saunders Company, Philadelphia (1998). Therefore, the methods of the invention are applicable to both prostate neoplastic conditions and prostate pathologies.

Therefore, the invention provides a method for both diagnosing and prognosing a prostate neoplastic condition including prostate cancer and prostate interepithelial neoplasia as well as other prostate pathologies such as BPH and prostatitis.

The invention also provides diagnostic methods relating to liver cancer. While PAMP expression is not observed in normal liver, expressed sequences corresponding to portions of PAMP have been isolated from tumor tissues such as hepatocellular carcinoma, and, to a lesser extent, invasive ovarian tumor, genitourinary tract tumors and endometrial adenocarcinoma. Furthermore, the 5.0 and 6.5 kb PAMP transcripts were expressed and testis and ovary tissues (see FIG. 3). These results indicate that elevated PAMP expression can be used to diagnose hepatocellular carcinoma, genitourinary tract tumors, endometrial adenocarcinoma, ovarian cancer and testicular cancer. One skilled in the art understands that the methods are practiced as described herein for prostate neoplastic conditions, with the sample chosen appropriately. For example, a sample containing liver cells is assayed according to a method of the invention for diagnosing or predicting susceptibility to liver cancer such as hepatocellular carcinoma.

Thus, the invention provides a method of diagnosing or predicting susceptibility to hepatocellular carcinoma in an individual by obtaining a sample from said individual; measuring a test expression level of PAMP in the sample; and comparing the test expression level of PAMP to a control expression level of PAMP, where a test expression level 2-fold or more greater than the control expression level indicates the presence of hepatocellular carcinoma.

The invention also provides a method of diagnosing or predicting susceptibility to ovarian cancer in an individual by obtaining a sample from said individual; measuring a test expression level of PAMP in the sample; and comparing the test expression level of PAMP to a control expression level of PAMP, where a test expression level 2-fold or more greater than the control expression level indicates the presence of ovarian cancer.

Thus, the invention provides a method of diagnosing or predicting susceptibility to testicular cancer in an individual by obtaining a sample from said individual; measuring a test expression level of PAMP in the sample; and comparing the test expression level of PAMP to a control expression level of PAMP, where a test expression level 2-fold or more greater than the control expression level indicates the presence of testicular cancer.

The invention provides a method of diagnosing or predicting prostate neoplastic conditions based on a finding of a positive correlation between a test expression level of PAMP in neoplastic cells of the prostate and the degree or extent of the neoplastic condition or pathology. The diagnostic methods of the invention are applicable to numerous prostate neoplastic conditions and pathologies as described above. One consequence of progression into these neoplastic and pathological conditions can be increased expression of PAMP in prostate tissue. The increase in PAMP expression in individuals suffering from a prostate neoplastic condition can be measured by comparing the amount of PAMP to that found, for example, in normal prostate tissue samples or in normal blood or serum samples. A two-fold or more increase in a test expression level in a prostate cell sample relative to a control expression sample obtained, for example, from normal prostate cells or from an androgen-dependent cell line is indicative of a prostate neoplastic condition or pathology. Similarly, an increase in PAMP expression leading to two-fold or more secretion into the blood or other circulatory fluids of the individual compared to control blood or fluid samples also can be indicative of a prostate neoplastic condition or pathology.

As a diagnostic indicator, PAMP can be used qualitatively to positively identify a prostate neoplastic condition or pathology as described above. Alternatively, PAMP also can be used quantitatively to determine the degree or susceptibility of a prostate neoplastic condition or pathology. For example, successive increases in the expression levels of PAMP can be used as a predictive indicator of the degree or severity of a prostate neoplastic condition or pathology. For example, increased expression can lead to a rise in accumulated levels and can be positively correlated with increased severity of a neoplastic condition of the prostate. A higher level of PAMP expression can be correlated with a later stage of a prostate neoplastic condition or pathology. For example, increases in expression levels of two-fold or more compared to a normal sample can be indicative of at least prostate neoplasia. PAMP also can be used quantitatively to distinguish between pathologies and neoplastic conditions as well as to distinguish between the different types of neoplastic conditions.

Correlative increases can be determined by comparison of PAMP expression from the individual having, or suspected of having, a neoplastic condition of the prostate to expression levels of PAMP from known samples determined to exhibit a prostate neoplastic condition. Alternatively, correlative increases also can be determined by comparison of a test expression level of PAMP expression to expression levels of other known markers of prostate cancer such as prostate specific antigen (PSA), glandular kallikrein 2 (hK2) and prostase/PRSS18. These other known markers can be used, for example, as an internal or external standard for correlation of stage-specific expression with increases in PAMP expression and severity of the neoplastic or pathological condition. Conversely, a regression in the severity of a prostate neoplastic condition or pathology can be followed by a corresponding decrease in PAMP expression levels and can similarly be assessed using the methods described herein.

Given the teachings and guidance provided herein, those skilled in the art will know or can determine the stage or severity of a prostate neoplastic condition or pathology based on a determination of PAMP expression and correlation with a prostate neoplastic condition or pathology. A correlation can be determined using known procedures and marker comparisons as described herein. For a review of recognized values for such other marker in normal versus pathological tissues, see, for example, *Campbell's Urology*, Seventh Edition, W.B. Saunders Company, Philadelphia (1998).

The use of PAMP expression levels in prostate cells, the circulatory system and urine as a diagnostic indicator of a prostate pathology allows for early diagnosis as a predictive indicator when no physiological or pathological symptoms are apparent. The methods are particularly applicable to any males over age 50, African-American males and males with familial history of prostate neoplastic conditions or pathologies. The diagnostic methods of the invention also are particularly applicable to individuals predicted to be at risk for prostate neoplastic conditions or pathologies by reliable prognostic indicators prior to onset of overt clinical symptoms. All that is necessary is to determine the PAMP prostate tissue or circulatory or bodily fluid expression levels to determine whether there is an increase in these PAMP levels in the individual suspected of having a prostate pathology compared to a control expression level such as the level observed in normal individuals. Those skilled in the art will know by using routine examinations and practices in the field of medicine those individuals who are applicable candidates for diagnosis by the methods of the invention.

For example, individuals suspected of having a prostate neoplastic condition or pathology can be identified by exhibiting presenting signs of prostate cancer which include, for example, a palpable nodule (>50% of the cases), dysuria, cystitis and prostatitis, frequency, urinary retention, or decreased urine stream. Signs of advanced disease include pain, uremia, weight loss and systemic bleeding. Prognostic methods of this invention are applicable to individuals after diagnosis of a prostate neoplastic condition, for example, to monitor improvements or identify residual neoplastic prostate cells using, for example, imaging methods known in the art and which target PAMP.

Therefore, the invention also provides a method of predicting the onset of a prostate neoplastic condition or pathology. The method consists of determining increased PAMP expression levels in a prostate cell sample or in fluids from an individual having or suspected of having a prostate neoplastic condition or pathology compared to a sample isolated from a normal individual, where increased PAMP expression in the sample indicates the onset of the prostate neoplastic condition or pathology.

The diagnostic methods of the invention are applicable for use with a variety of different types of samples isolated or obtained from an individual having, or suspected of having a prostate neoplastic condition or prostate pathology. For example, samples applicable for use in one or more diagnostic formats of the invention, include tissue and cell samples. A tissue or cell sample can be obtained, for example, by biopsy or surgery. As described below, and depending on the format of the method, the tissue can be used whole or subjected to various methods known in the art to disassociate the sample into smaller pieces, cell aggregates or individual cells. Additionally, when combined with amplification methods such as polymerase chain reaction (PCR), a single prostate cell sample is sufficient for use in diagnostic assays of the invention which employ hybridization detection methods. Similarly, when measuring PAMP polypeptide or activity levels, amplification of the signal with enzymatic coupling or photometric enhancement can be employed using only a few or a small number of cells.

Whole tissue obtained from a prostate biopsy or surgery is one example of a prostate cell sample. Whole tissue prostate cell samples can be assayed employing any of the formats described below. For example, the prostate tissue sample can be mounted and hybridized in situ with PAMP nucleic acid probes. Similar histological formats employing protein detection methods and in situ activity assays also can be used to detect a PAMP polypeptide in whole tissue prostate cell samples. Protein detection methods include, for example, staining with a PAMP specific antibody and activity assays. Such histological methods as well as others well known to those skilled in the art are applicable for use in the diagnostic methods of the invention using whole tissue as the source of a prostate cell sample. Methods for preparing and mounting the samples are similarly well known in the art.

Individual prostate cells and cell aggregates from an individual having, or suspected of having a prostate neoplastic condition or pathology is another example of a prostate cell sample which can be analyzed for increased expression of PAMP RNA, polypeptide or activity. The cells can be grown in culture and analyzed in situ using procedures such as those described above. Whole cell samples expressing cell surface markers associated with PAMP expression can be rapidly tested using fluorescent or magnetic activated cell sorting (FACS or MACS) with labeled binding agents selective for the surface marker or using binding agents selective for epithelial or prostate cell populations, for example, and then determining a test expression level of PAMP within this population. The test expression level can be determined using, for example, binding agents selective for PAMP or by hybridization to a PAMP specific probe. Other methods for measuring the expression level of PAMP in whole cell samples are known in the art and are similarly applicable in any of the diagnostic formats described below.

The tissue or whole cell prostate cell sample obtained from an individual also can be analyzed for increased PAMP expression by lysing the cell and measuring a test expression levels of PAMP in the lysate, a fractionated portion thereof or a purified component thereof using any of diagnostic formats described herein. For example, if a hybridization format is used, PAMP RNA can be amplified directly from the lysate using PCR, or other amplification procedures well known in the art such as RT-PCR, 5' or 3' RACE to directly measure the expression levels of PAMP nucleic acid molecules. RNA also can be isolated and probed directly such as by solution hybridization or indirectly by hybridization to immobilized RNA. Similarly, when determining a test expression level of PAMP using polypeptide detection formats, lysates can be assayed directly, or they can be further fractionated to enrich for PAMP and its corresponding activity. Numerous other methods applicable for use with whole prostate cell samples are well known to those skilled in the art and can accordingly be used in the methods of the invention.

The prostate tissue or cell sample can be obtained directly from the individual or, alternatively, it can be obtained from other sources for testing. Similarly, a cell sample can be tested when it is freshly isolated or it can be tested following short or prolonged periods of cryopreservation without substantial loss in accuracy or sensitivity. If the sample is to be tested following an indeterminate period of time, it can be obtained and then cryopreserved, or stored at 4° C. for short periods of time, for example. An advantage of the diagnostic methods of the invention is that they do not require histological analysis of the sample. As such, the sample can be initially disaggregated, lysed, fractionated or purified and the active component stored for later diagnosis.

The diagnostic methods of the invention are applicable for use with a variety of different types of samples other than prostate cell samples. For example, a PAMP polypeptide or fragment thereof that is released into the extracellular space, including circulatory fluids as well as other bodily fluids, can be used in diagnostic methods to detect a secreted polypeptide or fragment related to a PAMP polypeptide. In such a case, the diagnostic methods of the invention are applicable with fluid samples collected from an individual having, or suspected of having a neoplastic condition of the prostate or a prostate pathology.

Fluid samples, which can be measured for PAMP expression levels, include, for example, blood, serum, lymph, urine and semen. Other bodily fluids are known to those skilled in the art and are similarly applicable for use as a sample in the diagnostic methods of the invention. One advantage of analyzing fluid samples is that they are readily obtainable, in sufficient quantity, without invasive procedures as required by biopsy and surgery. Analysis of fluid samples such as blood, serum and urine will generally be in the diagnostic formats described herein which measure PAMP polypeptide levels or activity. As the PAMP related polypeptide is circulating in a soluble form, the methods will be similar to those which measure expression levels from cell lysates, fractionated portions thereof or purified components.

Prostate neoplastic conditions and prostate pathologies can be diagnosed, predicted or prognosed by measuring a test expression level of PAMP in a prostate cell sample, circulating fluid or other bodily fluid obtained from the individual. As described herein, expression levels can be measured by a variety methods known in the art. For example, a test expression level of PAMP can be determined by measuring the amount of PAMP RNA or polypeptide in a sample from the individual. Alternatively, a test expression level of PAMP can be determined by measuring the amount of a PAMP activity in the sample, the amount of activity being indicative of PAMP expression levels.

One skilled in the art can readily determine an appropriate assay system given the teachings and guidance provided herein and choose a method based on measuring RNA, polypeptide or activity. Considerations such as the sample type, availability and amount will also influence selection of a particular diagnostic format. For example, if the sample is a prostate cell sample and there is only a small amount available, then diagnostic formats which measure the amount of PAMP RNA by, for example, PCR amplification, or which measure PAMP-related cell surface polypeptide by, for example, FACS analysis can be appropriate choices for determining the expression level of PAMP. Alternatively, if the sample is a blood sample and the user is analysing numerous different samples simultaneous, such as in a clinical setting, then a multisample format, such as an Enzyme Linked Immunoabsorbant Assay (ELISA), which measures the amount of PAMP polypeptide can be an appropriate choice for determining the expression level of PAMP. Additionally, PAMP nucleic acid molecules released into bodily fluids from the neoplastic or pathological prostate cells can also be analyzed by, for example, PCR or RT-PCR. Those skilled in the art will know, or can determine which format is amenable for a particular application and which methods or modifications known within the art are compatible with a particular type of format.

Hybridization methods are applicable for measuring the amount of PAMP RNA as an indicator of PAMP expression levels. There are numerous methods well known in the art for detecting nucleic acid molecules by specific or selective hybridization with a complementary probe. Such methods include both solution hybridization procedures and solid-phase hybridization procedures where the probe or sample is immobilized to a solid support. Descriptions for such methods can be found in, for example, Sambrook et al., supra, and in Ausubel et al., supra. Specific examples of such methods include PCR and other amplification methods such as RT-PCR, 5' or 3' RACE, RNase protection, RNA blot, dot blot or other membrane-based technologies, dip stick, pin, ELISA or two-dimensional arrays immobilized onto chips as a solid support. These methods can be performed using either qualitative or quantitative measurements, all of which are well known to those skilled in the art.

PCR or RT-PCR can be used with isolated RNA or crude cell lysate preparations. As described previously, PCR is advantageous when there is limiting amounts of starting material. A further description of PCR methods can be found in, for example, Dieffenbach, C. W., and Dveksler, G. S., *PCR Primer: A Laboratory Manual*, Cold Spring Harbor Press, Plainview, N.Y. (1995). Multisample formats such as an ELISA or two-dimensional array offer the advantage of analyzing numerous, different samples in a single assay. A particular example of a two-dimentional array used in a hybridization format is described further below in the Examples. In contrast, solid-phase dip stick-based methods offer the advantage of being able to rapidly analyze a patient's fluid sample and obtain an immediate result.

Nucleic acid probes useful for measuring the expression level of PAMP by hybridization include, for example, all of the PAMP nucleic acid probes described herein. More specifically, such probes include, for example, nucleic acid molecules corresponding to the entire PAMP cDNA (SEQ ID NO:1) and fragments thereof. Smaller fragments thereof also can be used, including oligonucleotides corresponding to PAMP nucleotide sequences and which are capable of specifically or selectively hybridizing to PAMP RNA. In a preferred embodiment, the diagnostic methods of the invention employ a PAMP nucleic acid probe that contains at least 10 contiguous nucleotides of SEQ ID NO:1, where the contiguous nucleotides include at least one nucleotide of the nucleotide sequence shown as position 1 to position 3221 of SEQ ID NO:1, provided that the probe does not have the nucleotide sequence of AA363808, AW959484, BE165930, nucleotides 1 to 614 of BE893201 or nucleotides 1 to 1530 of AK026780.

Briefly, for detection by hybridization, the PAMP nucleic acid probes having detectable labels are added to a prostate cell sample or a fluid sample obtained from the individual having, or suspected of having a prostate neoplastic condition or pathology under conditions which allow annealing of the probe to PAMP RNA. Methods for detecting PAMP RNA in a sample can include the use of, for example, RT-PCR. Conditions are well known in the art for both solution and solid phase hybridization procedures. Moreover, optimization of hybridization conditions can be performed, if desired, by hybridization of an aliquot of the sample at different temperatures, durations and in different buffer conditions. Such procedures are routine and well known to those skilled. Following annealing, the sample is washed and the signal is measured and compared with a suitable control or standard value. The magnitude of the hybridization signal is directly proportional to the expression levels of PAMP.

A test expression level is compared to a suitable control expression level, which can be, for example, the expression level of PAMP from a prostate cell or a fluid sample obtained from a normal individual. Another suitable control for comparison is a prostate cell line that is androgen-dependent. PAMP expression levels in cell lines should be determined under androgen depleted growth conditions, as their response to androgen stimulation will be indicative of PAMP expression levels in neoplastic cells. The control expression level can be determined simultaneously with one or more test samples or, alternatively, expression levels can be established for a particular type of sample and standardized to internal or external parameters such as protein or nucleic acid content, cell number or mass of tissue. Such standardized control samples can then be directly compared with results obtained from the test sample. An increase of two-fold or more of a test expression level of PAMP indicates the presence of a prostate neoplastic condition or pathology in the tested individual.

The diagnostic procedures described herein can additionally be used in conjunction with other prostate markers, such as prostate specific antigen, human glandular kallikrein 2 (hk2) and prostase/PRSS18 for simultaneous or independent corroboration of a sample. Additionally, PAMP can be used, for example, in combination with other markers to further distinguish normal basal cells, secretory cells and neoplastic cells of the prostate. Moreover, PAMP expression can be used in conjunction with smooth muscle cell markers to distinguish between pathological conditions such as benign prostate hypertrophy (BPH) and neoplasia. Those skilled in the art will know which markers are applicable for use in conjunction with PAMP to delineate more specific diagnostic information such as that described above.

The invention additionally provides a method of diagnosing or predicting the susceptibility of a prostate neoplastic condition in an individual suspected of having a neoplastic condition of the prostate where PAMP expression level is determined by measuring the amount of PAMP polypeptide. The method consists of contacting a cell, a cell lysate, or fractionated sample thereof, from the individual with a binding agent selective for PAMP, and determining the amount of selective binding of the agent. In one embodiment, the binding agent is an antibody.

In one embodiment, a test expression level is determined by measuring the amount of PAMP polypeptide using a binding agent selective for PAMP polypeptide residues 1 to 1074 of SEQ ID NO:2. In a further embodiment, a test expression level is determined by measuring the amount of PAMP polypeptide using an antibody selective for PAMP polypeptide residues 1 to 1074 of SEQ ID NO:2.

Essentially all modes of affinity binding assays are applicable for use in determining a test expression level of a PAMP polypeptide in a sample. Such methods are rapid, efficient and sensitive. Moreover, affinity binding methods are simple and can be modified to be performed under a variety of clinical settings and conditions to suit a variety of particular needs. Affinity binding assays which are known and can be used in the methods of the invention include both soluble and solid phase formats. A specific example of a soluble phase affinity binding assay is immunoprecipitation using a PAMP selective antibody or other binding agent. Solid phase formats are advantageous for the methods of the invention since they are rapid and can be performed more easily on multiple different samples simultaneously without losing sensitivity or accuracy. Moreover, solid phase affinity binding assays are further amenable to high throughput screening and automation.

Specific examples of solid phase affinity binding assays include immunoaffinity binding assays such as an ELISA and radioimmune assay (RIA). Other solid phase affinity binding assays are known to those skilled in the art and are applicable to the methods of the invention. Although affinity binding assays are generally formatted for use with an antibody binding molecules that is selective for the analyte or ligand of interest, essentially any binding agent can be alternatively substituted for the selectively binding antibody. Such binding agents include, for example, macromolecules such as polypeptides, peptides, nucleic acid molecules, lipids and sugars as well as small molecule compounds. Methods are known in the art for identifying such molecules which bind selectively to a particular analyte or ligand and include, for example, surface display libraries and combinatorial libraries. Thus, for a molecule other than an antibody to be used in an affinity binding assay, all that is necessary is for the binding agent to exhibit selective binding activity for PAMP.

Various modes of affinity binding formats are similarly known which can be used in the diagnostic methods of the invention. For the purpose of illustration, particular embodiments of such affinity binding assays will be described further in reference to immunoaffinity binding assays. The various modes of affinity binding assays, such as immunoaffinity binding assays, include, for example, solid phase ELISA and RIA as well as modifications thereof. Such modifications thereof include, for example, capture assays and sandwich assays as well as the use of either mode in combination with a competition assay format. The choice of which mode or format of immunoaffinity binding assay to use will depend on the intent of the user. Such methods can be found described in common laboratory manuals such as Harlow and Lane, *Using Antibodies: A Laboratory Manual*, Cold Spring Harbor Laboratory Press, New York (1999).

As with the hybridization methods described previously, the diagnostic formats employing affinity binding can be used in conjunction with a variety of detection labels and systems known in the art to quantitate amounts of PAMP in the analyzed sample. Detection systems include the detection of bound PAMP by both direct and indirect means. Direct detection methods include labeling of the PAMP-selective antibody or binding agent. Indirect detection systems include, for example, the use of labeled secondary antibodies and binding agents.

Secondary antibodies, labels and detection systems are well known in the art and can be obtained commercially or by techniques well known in the art. The detectable labels and systems employed with the PAMP-selective binding agent should not impair binding of the agent to PAMP. Moreover, multiple antibody and label systems can be employed for detecting the bound PAMP-selective antibody to enhance the sensitivity of the binding assay if desired.

As with the hybridization formats described previously, detectable labels can be essentially any label that can be quantitated or measured by analytical methods. Such labels include, for example, enzymes, radioisotopes, fluorochromes as well as chemi- and bioluminescent compounds. Specific examples of enzyme labels include horseradish peroxidase (HRP), alkaline phosphatase (AP), β-galactosidase, urease and luciferase.

A horseradish-peroxidase detection system can be used, for example, with the chromogenic substrate tetramethylbenzidine (TMB), which yields a soluble product in the presence of hydrogen peroxide that is detectable by measuring absorbance at 450 nm. An alkaline phosphatase detection system can be used with the chromogenic substrate p-nitrophenyl phosphate, for example, which yields a soluble product readily detectable by measuring absorbance at 405 nm. Similarly, a β-galactosidase detection system can be used with the chromogenic substrate o-nitrophenyl-β-D-galactopyranoside (ONPG), which yields a soluble product detectable by measuring absorbance at 410 nm, or a urease detection system can be used with a substrate such as urea-bromocresol purple (Sigma Immunochemicals, St. Louis, Mo.). Luciferin is the substrate compound for luciferase which emits light following ATP-dependent oxidation.

Fluorochrome detection labels are rendered detectable through the emission of light of ultraviolet or visible wavelength after excitation by light or another energy source. DAPI, fluorescein, Hoechst 33258, R-phycocyanin, B-phycoerythrin, R-phycoerythrin, rhodamine, Texas red and lissamine are specific examples of fluorochrome detection labels that can be utilized in the affinity binding formats of the invention. A particularly useful fluorochrome is fluorescein or rhodamine.

Chemiluminescent as well as bioluminescent detection labels are convenient for sensitive, non-radioactive detection of PAMP and can be obtained commercially from various sources such as Amersham Lifesciences, Inc. (Arlington Heights, Ill.).

Alternatively, radioisotopes can be used as detectable labels in the methods of the invention. Iodine-125 is a specific example of a radioisotope useful as a detectable label.

Signals from detectable labels can be analyzed, for example, using a spectrophotometer to detect color from a chromogenic substrate; a fluorometer to detect fluorescence in the presence of light of a certain wavelength; or a radiation counter to detect radiation, such as a gamma counter for detection of iodine-125. For detection of an enzyme-linked secondary antibody, for example, a quantitative analysis of the amount of bound agent can be made using a spectrophotometer such as an EMAX Microplate Reader (Molecular Devices, Menlo Park, Calif.) in accordance with the manufacturer's instructions. If desired, the assays of the invention can be automated or performed robotically, and the signal from multiple samples can be detected simultaneously.

The diagnostic formats of the present invention can be forward, reverse or simultaneous as described in U.S. Pat. No. 4,376,110 and No. 4,778,751. Separation steps for the various assay formats described herein, including the removal of unbound secondary antibody, can be performed by methods known in the art (Harlow and Lane, supra). For example, washing with a suitable buffer can be followed by filtration, aspiration, vacuum or magnetic separation as well as by centrifugation.

A binding agent selective for PAMP also can be utilized in imaging methods that are targeted at PAMP expressing prostate cells. These imaging techniques will have utility in identification of residual neoplastic cells at the primary site following standard treatments including, for example, radical prostatectomy, radiation or hormone therapy. In addition, imaging techniques that detect neoplastic prostate cells have utility in detecting secondary sites of metastasis. The PAMP specific binding agent can be radiolabeled with, for example, indium and infused intravenously as described by Kahn et al., *Journal of Urology* 152:1952-1955 (1994). The binding agent selective for PAMP can be, for example, a monoclonal antibody selective for PAMP polypeptide. Imaging can be accomplished by, for example, radioimmunoscintigraphy as described by Kahn et al., supra.

The invention additionally provides a method of diagnosing or predicting the susceptibility of a prostate neoplastic condition in an individual suspected of having a neoplastic condition of the prostate, where a test expression level of PAMP is determined by measuring the amount of PAMP activity. The method consists of contacting a cell, a cell lysate, or fractionated sample thereof, from the individual with an agent that functions to measure an activity associated with PAMP.

Another diagnostic format which can be used for determining the expression levels of PAMP is by measuring an activity associated with a PAMP polypeptide. As with the hybridization and affinity binding formats, activity assays can similarly be performed using essentially identical methods and modes of analysis. Therefore, solution and solid phase modes, including multisample ELISA, RIA and two-dimentional array procedures are applicable for use in measuring an activity associated with PAMP. The activity can be measured by, for example, incubating an agent that functions to measure an activity associated with PAMP with the sample and determining the amount of product formed that corresponds to a PAMP activity. The amount of product formed will directly correlate with the PAMP activity in the sample and therefore, with the expression levels of PAMP in the sample.

The invention further provides a method of identifying a compound that inhibits the PAMP activity. The method consists of contacting a sample containing PAMP and an agent that functions to measure an activity associated with PAMP with a test compound under conditions that allow formation of a product that corresponds to a PAMP activity and measuring the amount of product formed, wherein a decrease in the amount of product formed in the presence of the test compound compared to the absence of the test compound indicates that the compound has PAMP inhibitory activity. Similarly, compounds that increase the activity of PAMP also can be identified. A test compound added to a sample containing PAMP and an agent that functions to measure an activity associated with PAMP which increases the amount of product formed compared to the absence of the test compound indicates that the compound increases PAMP activity. Therefore, the invention provides a method of identifying compounds that modulate the activity of PAMP. The PAMP containing sample used for such a method can be serum, prostate tissue, a prostate cell population or a recombinant cell population expressing PAMP.

Those compounds having inhibitory activity are considered as potential PAMP antagonists and further as potential therapeutic agents for treatment of neoplastic conditions of the prostate. Similarly, those compounds which increase a PAMP activity are considered as potential PAMP agonists and further as potential therapeutic agents for the treatment of neoplastic conditions of the prostate.

Within the biological arts, the term "about" when used in reference to a particular activity or measurement is intended to refer to the referenced activity or measurement as being within a range of values encompassing the referenced value and within accepted standards of a credible assay within the art, or within accepted statistical variance of a credible assay within the art.

A reaction system for identifying a compound that inhibits or enhances PAMP activity can be performed using essentially any source of PAMP activity. Such sources include, for example, a prostate cell sample, lysate or fractionated portion thereof; a bodily fluid such as blood, serum or urine from an individual with a prostate neoplastic condition; a recombinant cell or soluble recombinant source, and an in vitro translated source. The PAMP source is combined with an agent that functions to measure an activity associated with PAMP as described above and incubated in the presence or absence of a test inhibitory compound. The amount of product that corresponds to a PAMP activity that is formed in the presence of the test compound is compared with that in the absence of the test compound. Those test compounds which provide inhibition of product formation of at least about 50% are considered to be PAMP inhibitors. Similarly, those compounds which increase product formation of two-fold or more are considered to be PAMP enhancers or activators. PAMP inhibitors can then be subjected to further in vitro or in vivo testing to confirm that they inhibit a PAMP activity in cellular and animal models.

Suitable test compounds for the inhibition or enhancement assays can be any substance, molecule, compound, mixture of molecules or compounds, or any other composition which is suspected of being capable of inhibiting PAMP activity in vivo or in vitro. The test compounds can be macromolecules, such as biological polymers, including proteins, polysaccharides and nucleic acid molecules. Sources of test compounds which can be screened for PAMP inhibitory activity include, for example, libraries of peptides, polypeptides, DNA, RNA and small organic compounds. The test compounds can be selected randomly and tested by the screening methods of the present invention. Test compounds are administered to the reaction system at a concentration in the range from about 1 nM to 1 mM.

Methods for producing pluralities of compounds to use in screening for compounds that modulate the activity of a PAMP polypeptide, including chemical or biological molecules that are inhibitors or enhancers of PAMP activity such as simple or complex organic molecules, metal-containing compounds, carbohydrates, peptides, proteins, peptidomimetics, glycoproteins, lipoproteins, nucleic acid molecules, antibodies, and the like, are well known in the art and are described, for example, in Huse, U.S. Pat. No. 5,264,563; Francis et al., *Curr. Opin. Chem. Biol.* 2:422-428 (1998); Tietze et al., *Curr. Biol.*, 2:363-371 (1998); Sofia, *Mol. Divers.* 3:75-94 (1998); Eichler et al., *Med. Res. Rev.* 15:481-496 (1995); and the like. Libraries containing large numbers of natural and synthetic compounds also can be obtained from commercial sources. Combinatorial libraries of molecules can be prepared using well known combinatorial chemistry methods (Gordon et al., *J. Med. Chem.* 37: 1233-1251 (1994); Gordon et al., *J. Med. Chem.* 37: 1385-1401 (1994); Gordon et al., *Acc. Chem. Res.* 29:144-154 (1996); Wilson and Czarnik, eds., *Combinatorial Chemistry: Synthesis and Application*, John Wiley & Sons, New York (1997)).

Therefore, the invention provides a method of identifying a compound that inhibits or enhances
a PAMP activity where the sample further consists of a prostate cell lysate, a recombinant cell lysate expressing PAMP, an in vitro translation lysate containing PAMP mRNA, a fractionated sample of a prostate cell lysate, a fractionated sample of a recombinant cell lysate expressing PAMP, a fractionated sample of an in vitro translation lysate containing PAMP mRNA or an isolated PAMP polypeptide. The method can be performed in single or multiple sample format.

In another embodiment, PAMP polypeptides and PAMP peptides can be used as vaccines to prophylactically treat individuals for the occurrence of a prostate neoplastic condition or pathology. Such vaccines can be used to induce B or T cell immune responses or both aspects of the individuals endogenous immune mechanisms. The mode of administration and formulations to induce either or both of these immune responses are well known to those skilled in the art. For example, PAMP polypeptides and peptides can be administered in many possible formulations, including pharmaceutically acceptable mediums. They can be administered alone or, for example, in the case of a peptide, the peptide can be conjugated to a carrier, such as KLH, in order to increase its immunogenicity. The vaccine can include or be administered in conjunction with an adjuvant, various of which are known to those skilled in the art. After initial immunization with the vaccine, further boosters can be provided if desired. Therefore, the vaccines are administered by conventional methods in dosages which are sufficient to elicit an immunological response, which can be easily determined by those skilled in the art. Alternatively, the vaccines can comprise anti-idiotypic antibodies which are internal images of the PAMP polypeptides and peptides described above. Methods of making, selecting and administering such anti-idiotype vaccines are well known in the art. See, for example, Eichmann, et al., CRC Critical Reviews in Immunology 7:193-227 (1987). In addition, the vaccines can comprise a nucleic acid molecule encoding PAMP, for example, substantially the nucleotide sequence shown as SEQ ID NO:1. Methods for using nucleic acid molecules such as DNA as vaccines are well known to those skilled in the art (see, for example, Donnelly et al. (*Ann. Rev. Immunol.* 15:617-648 (1997)); Felgner et al. (U.S. Pat. No. 5,580,859, issued Dec. 3, 1996); Felgner (U.S. Pat. No. 5,703,055, issued Dec. 30, 1997); and Carson et al. (U.S. Pat. No. 5,679,647, issued Oct. 21, 1997)).

The invention additionally provides a method of treating or reducing the progression of a prostate neoplastic condition. The method consists of administering to an individual having a neoplastic condition of the prostate an inhibitory amount of a PAMP specific inhibitor, wherein said inhibitory amount causes a reduction of at least about 2-fold in the amount or activity of PAMP. A specific example of a PAMP specific inhibitor is a PAMP nucleic acid molecule. PAMP inhibitors, including antibodies, antisense nucleic acid molecules and compounds identified by the methods described herein can therefore be used as therapeutics for treating or reducing the severity of an individual with a prostate neoplastic condition or pathology.

As used herein, the term "inhibitor" is intended to refer to an agent effecting a decrease in the extent, amount or rate of PAMP expression or effecting a decrease in the activity of a PAMP polypeptide activity. An example of a PAMP inhibitor which effects a decrease in PAMP expression includes PAMP antisense nucleic acid molecules and transcriptional inhibitors that bind to the PAMP 5' promoter/regulatory region.

As used herein, the term "inhibitory amount" is intended to refer to the amount of an inhibitor necessary to effect a reduction of at least about 2-fold in the extent, amount or rate of PAMP expression.

Such inhibitors can be produced using methods which are generally known in the art, and include the use of purified PAMP polypeptide to produce antibodies or to screen libraries of compounds, as described previously, for those which specifically bind PAMP. For example, in one aspect, antibodies which are selective for PAMP can be used directly as an antagonist, or indirectly as a targeting or delivery mechanism for bringing a cytotoxic or cytostatic agent to neoplastic prostate cells. Such agents can be, for example, radioisotopes. The antibodies can be generated using methods that are well known in the art and include, for example, polyclonal, monoclonal, chimeric, humanized single chain, Fab fragments, and fragments produced by a Fab expression library.

As used herein, the term "functional fragment" when used in reference to a 5' promoter and regulatory region of PAMP is intended to refer to a portion of the promoter and regulatory region having at least one of the activities of its parent nucleic acid molecule. For example, a functional fragment can be a transcriptional regulatory element in a PAMP gene promoter or enhancer.

In another embodiment of the invention, the polynucleotides encoding PAMP, or any fragment thereof, or antisense molecules, can be used for therapeutic purposes. In one aspect, antisense molecules to the PAMP encoding nucleic acid molecules can be used to block the transcription or translation of the mRNA. Specifically, cells can be transformed with sequences complementary to PAMP nucleic acid molecules. Such methods are well known in the art, and sense or antisense oligonucleotides or larger fragments, can be designed from various locations along the coding or control regions of sequences encoding PAMP. Thus, antisense molecules may be used to modulate PAMP activity, or to achieve regulation of gene function.

Expression vectors derived from retroviruses, adenovirus, adeno-associated virus (AAV), herpes or vaccinia viruses, or from various bacterial plasmids can be used for delivery of antisense nucleotide sequences to the prostate cell population. The viral vector selected should be able to infect the tumor cells and be safe to the host and cause minimal cell transformation. Retroviral vectors and adenoviruses offer an efficient, useful, and presently the best-characterized means of introducing and expressing foreign genes efficiently in mammalian cells. These vectors are well known in the art and have very broad host and cell type ranges, express genes stably and efficiently. Methods which are well known to those skilled in the art can be used to construct such recombinant vectors and are described in Sambrook et al. (supra). Even in the absence of integration into the DNA, such vectors can continue to transcribe RNA molecules until they are disabled by endogenous nucleases. Transient expression can last for a month or more with a non-replicating vector and even longer if appropriate replication elements are part of the vector system.

Ribozymes, enzymatic RNA molecules, can also be used to catalyze the specific cleavage of PAMP mRNA. The mechanism of ribozyme action involves sequence-specific hybridization of the ribozyme molecule to complementary target PAMP RNA, followed by endonucleolytic cleavage. Specific ribozyme cleavage sites within any potential RNA target are identified by scanning the PAMP RNA for ribozyme cleavage sites which include the following sequences: GUA, GUU, and GUC. Once identified, short RNA sequences of between 15 and 20 ribonucleotides corresponding to the region of the target gene containing the cleavage site can be evaluated for secondary structural features which can render the oligonucleotide inoperable. The suitability of candidate targets can also be evaluated by testing accessibility to hybridization with complementary oligonucleotides using ribonuclease protection assays. Antisense molecules and ribozymes of the invention can be prepared by any method known in the art for the synthesis of nucleic acid molecules.

In another embodiment, the PAMP promoter and regulatory region can be used for constructing vectors for prostate cancer gene therapy. The promoter and regulatory region can be fused to a therapeutic gene for prostate specific expression. This method can include the addition of one or more enhancer elements which amplify expression of the heterologous therapeutic gene without compromising tissue specificity. Methods for identifying the PAMP gene promoter and regulatory region are well known to those skilled in the art, for example, by selecting an appropriate primer from the 5' end of the coding sequence and isolating the promoter and regulatory region from genomic DNA.

Examples of therapeutic genes that are candidates for prostate gene therapy utilizing the PAMP promoter include suicide genes. The expression of suicide genes produces a protein or agent that directly or indirectly inhibits neoplastic prostate cell growth or promotes neoplastic prostate cell death. Suicide genes include genes encoding enzymes, oncogenes, tumor suppressor genes, genes encoding toxins, genes encoding cytokines, or a gene encoding oncostatin. The therapeutic gene can be expressed using the vectors described previously for antisense expression.

In accordance with another embodiment of the present invention, there are provided diagnostic systems, preferably in kit form, comprising at least one invention nucleic acid molecule or antibody in a suitable packaging material. The diagnostic kits containing nucleic acid molecules are derived from the PAMP-encoding nucleic acid molecules described herein. In one embodiment, for example, the diagnostic nucleic acid molecules are derived from SEQ ID NO:1 and can be oligonucleotides or probes of the invention. Invention diagnostic systems are useful for assaying for the presence or absence of nucleic acid encoding PAMP in either genomic DNA or mRNA.

A suitable diagnostic system includes at least one invention nucleic acid molecule or antibody, as a separately packaged chemical reagent(s) in an amount sufficient for at least one assay. For a diagnostic kit containing a nucleic acid molecule of the invention, the kit will generally contain two or more nucleic acid molecules. When the diagnostic kit is to be used in PCR, the kit will contain at least two oligonucleotides that can serve as primers for PCR. Those of skill in the art can readily incorporate invention nucleic probes and/or primers or invention antibodies into kit form in combination with appropriate buffers and solutions for the practice of the invention methods as described herein. A kit containing a PAMP polypeptide-specific antibody can contain a reaction cocktail that provides the proper conditions for performing an assay, for example, an ELISA or other immunoassay, for determining the level of expression of a PAMP polypeptide in a sample, and can contain control samples that contain known amounts of a PAMP polypeptide and, if desired, a second antibody selective for the anti-PAMP antibody.

The contents of the kit of the invention, for example, PAMP nucleic acid molecules or antibodies, are contained in packaging material, preferably to provide a sterile, contaminant-free environment. In addition, the packaging material contains instructions indicating how the materials within the kit can be employed both to detect the presence or absence of a particular PAMP nucleic acid sequence or PAMP polypeptide or to diagnose the presence of, or a predisposition for a condition associated with the presence or absence of PAMP such as prostate cancer. The instructions for use typically include a tangible expression describing the reagent concentration or at least one assay method parameter, such as the relative amounts of reagent and sample to be admixed, maintenance time periods for reagent/sample admixtures, temperature, buffer conditions, and the like.

It is understood that modifications which do not substantially affect the activity of the various embodiments of this invention are also included within the definition of the invention provided herein. Accordingly, the following examples are intended to illustrate but not limit the present invention.

EXAMPLE I

Isolation of Full-length PAMP cDNA

This example describes the isolation of a full-length PAMP cDNA.

Rapid amplification of cDNA ends was performed as follows to isolate the full-length PAMP cDNA. Human prostate Marathon-ready cDNA (ClonTech; Palo Alto, Calif.) was used for RACE. cDNAs were also prepared from androgen stimulated LNCaP cells using the Marathon cDNA amplification kit (ClonTech) according to manufacturer's protocol and used for 5'-RACE. RACE primers were as follows: 9E1-594r (5'-TTTTGTATTTGGCATCTATTTTGCTGCGG-3'; SEQ ID NO:3), 9E1-669r (5'-TGCAGAATGGACATG-GAGTCGTGG-3'; SEQ ID NO:4), 9E1-RC52 (5'-GCTGG-GATGCTTGAGGGCTTGG-3'; SEQ ID NO: 5), 9E1-RC61 (5'-AAGGACCCTGCTGGGATGCTTGAG-3'; SEQ ID NO: 6). RACE reactions were performed according to the standard ClonTech protocol, and the resulting nucleic acids sequenced by standard methods.

As shown in FIG. 1, the full-length PAMP cDNA contains 4485 nucleotides predicted to encode a protein of 1382 amino acids.

Using the TMPRED protein prediction program, (www.ch.embnet.org/cgi-bin/TMPRED form parser), the PAMP sequence shown in FIG. 1 was predicted to contain at least 4 transmembrane domains. These domains are TM1 from amino acid 10 to amino acid 30 (21 residues); TM2 from amino acid 142 to amino acid 164 (23 residues); TM3 from amino acid 283 to amino acid 299 (17 residues); and TM4 from amino acid 430 to amino acid 452 (23 residues).

EXAMPLE II

Characterization of Androgen-regulated and Prostate-localized Expression of PAMP This example confirms that expression of PAMP is androgen-regulated and that PAMP is highly expressed in normal and neoplastic prostate epithelium relative to other human tissues.

A. Androgen-regulated Expression of PAMP

PAMP expression was studied in the prostate carcinoma cell line LNCaP. Androgen-regulated expression of PAMP was confirmed by Northern analysis using LNCaP RNA. The prostate carcinoma cell line LNCaP was cultured in RPM1 1640 medium supplemented with 10% fetal calf serum (FCS) (Life Technologies, Germantown, Md.). Twenty-four hours before androgen regulation experiments, LNCaP cells were transferred into RPMI 1640 media with 10% charcoal-stripped FCS(CS-FCS) (Life Technologies, Germantown, Md.). Media was replaced with fresh CS-FCS media or CS-FCS supplemented with 1 nM of the synthetic androgen R1881 (NEN Life Science Products Inc.; Boston, Mass.). Cells were harvested for RNA isolation at 0, 4, 8, 12, 16, 24, 36 and 48 hour time points.

Northern analysis was performed with total RNA isolated from the cells at the indicated time points. Briefly, the LNCaP RNA was isolated using TRIzol (Life Technologies; Germantown, Md.) according to the manufacturer's directions. A cDNA fragment containing nucleotides 3363 to 4485 of SEQ ID NO: 1 was labeled with [$\alpha$-$^{32}$P] dCTP (Amersham) using rediprime II random primer labelling system (Amersham), and the probes purified with Sephadex G50 Nick column (Pharmacia). The RNA blot was prepared by fractionating 10 µg total RNAs on a 1.2% formaldehyde gel and blotting (Sambrook et al., 1989). Northern hybridization was carried out in ExpressHyb™ hybridization solution (ClonTech). Northern blots were exposed to a phosphor screen (Molecular Dynamics), and the images were scanned into a computer with a Phosphorimager. Quantification was performed using ImageQuant program (Molecular Dynamics).

Figure 2B:
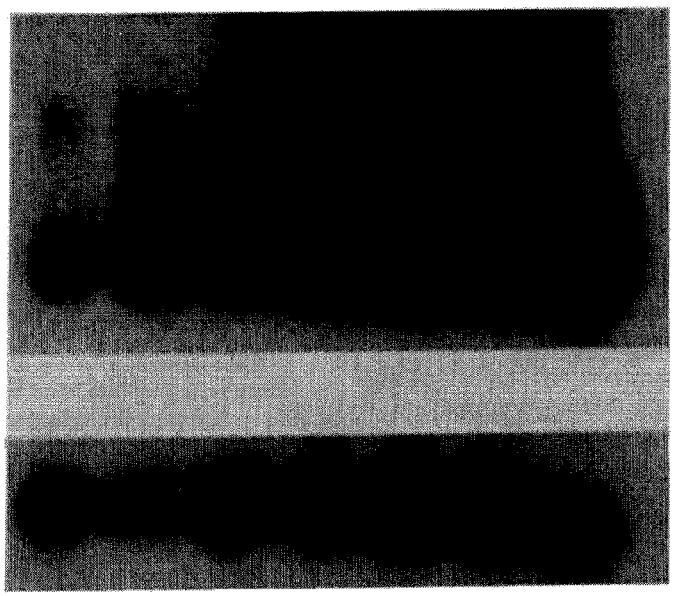

Phosphorimage quantitation of the Northern demonstrated an induction of PAMP expression that was maintained as up to 48 hours of androgen exposure with synthetic androgen R1881 (FIG. 2). PAMP expression could be detected after 4 hours of androgen supplementation and increased steadily through the 48-hour time point. These results demonstrate that expression of PAMP is induced by androgens.

B. Distribution of PAMP in Fetal and Adult Human Tissues

Figure 3A:
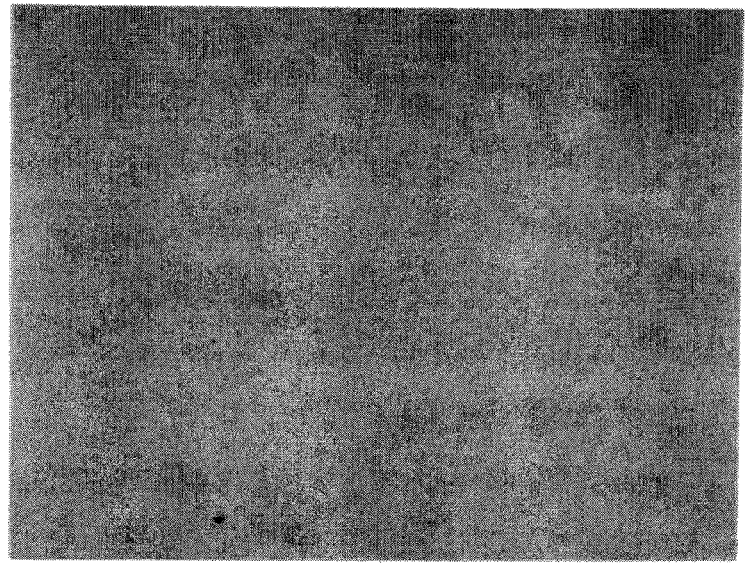
FIG. 3 shows analysis of PAMP expression using two multiple tissue northern blots (MTN) from ClonTech (Palo Alto, Calif.).
Figure 3B:
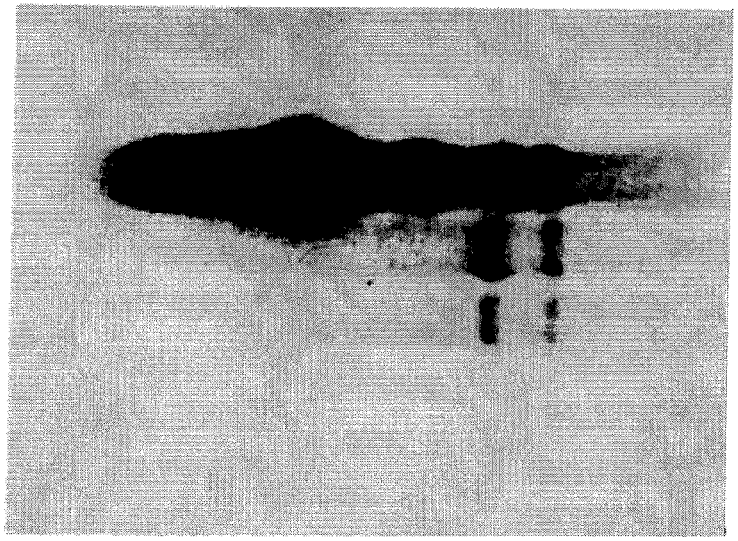

The distribution of PAMP transcripts in normal human tissues was also determined by Northern analysis performed as described above using a multiple tissue northern blot purchased from ClonTech and contained 2 µg of (poly)A+ RNA in each lane. A $\beta$-actin control probe was used to verify equivalent loading of RNA. FIG. 3 shows northern analysis of PAMP expression in 16 adult human tissues. Four forms of PAMP were observed. In 16 adult tissues examined, the 2.0 and 3.2 kb PAMP transcripts were predominantly expressed in prostate tissues, with very low or no detectable expression levels in heart, brain, placenta, lung, liver, skeletal muscle, kidney, pancreas, spleen, thymus, testes, ovary, small intestine, colon, or peripheral leukocytes (see FIG. 3). Two higher molecular weight forms of about 5.0 and 6.5 kb were also expressed in ovary and testis tissues.

Hybridization of PAMP to a multiple tissue expression (MTE) array containing 50 human tissues (ClonTech), both fetal and adult was performed as described above using the same probe. As shown in FIG. 4, the only significant hybridization was to grid C7, which contains human prostate tissue.

Together with the results described above, these results demonstrate that PAMP is a prostate-specific gene that is induced by androgen.

EXAMPLE III

In Situ Hybridization Analysis

This example describes in situ hybridization analysis and shows that PAMP is expressed in epithelial cells in both normal prostate and prostate cancer cells.

A PCR product was generated from the 3' end of the ARSDR1 using primer 9E1insitu1 (5'-TGAAGAACTCT-GCTTTCAGCTTCGC-3'; SEQ ID NO:7) and 9E1insitu2 (5'-AGGAAACAGCCTCCTGTGGAAAATG-3'; SEQ ID NO:8). The PCR product was cloned into vector PCRII-TOPO (Invitrogen) and subsequently linearized at either end with BamHI or EcoRV, and transcribed to generate sense and anti-sense digoxigenin-labeled probes. Both dig-dUTP labeled sense and anti-sense probe were prepared using a dig RNA labeling kit (Boehringer Mannheim) according to manufacturer's instructions.

In situ hybridization was performed on an automated instrument (Ventana Gen II, Ventana Medical Systems) essentially as follows. Formalin-fixed and paraffin-embedded prostate specimens were obtained from a previously surgical specimen tissue bank. Tissue sections (5 µm) were mounted onto Proma plus slides (VWR Scientific); deparaffinizeded in a 65° C. oven for 2 hours; soaked three times (5 minutes each) in xylene; and rehydrated through graded alcohol with a final rinse in 2×SSC. Before hybridization, sections were digested with proteinase I cocktail for 12 minutes at 37° C. Subsequently, 10 ng of either sense or anti-sense probe was applied in hybridization buffer. The probe was denatured at 65° C. for 4 minutes and hybridization was carried out at 42° C. for 360 minutes. The tissue sections were then rinsed with 2×, 1× and 0.1×SSC at 37° C. Hybridized probe was detected with mouse anti-dig antibody, and the signal amplified by consecutive application of biotin conjugated anti-mouse antibody and streptavidin-horseradish peroxidase. The in situ signal was visualized by DAB and counter-stained with hematoxylin.

The results of the in situ analysis are shown in FIG. 5. As evidenced by the staining seen in panel A (antisense PAMP probe; prostate cancer tissue sample) and panel C (antisense PAMP probe; normal prostate gland tissue sample), PAMP is expressed in epithelial cells in both normal prostate and prostate cancer cells.

EXAMPLE IV

Chromosomal Localization of PAMP Gene

These results demonstrate that PAMP is localized to chromosome 4p15-4p11 between markers D4S756 and D4S174.

The medium-resolution Stanford G3 radiation hybrid panel was used to map the chromosomal localization of ARSDR1 with primers 9E1MapF (5'-ACGTGCAGATA-CAATGCTCCTGAG-3'; SEQ ID NO:9) and 9E1MapR (5'-CATGTCATCGTTTTGCCACCG-3'; SEQ ID NO:10). The PCR conditions were 35 cycles of 94□C 30 seconds, 55 □C 30 seconds and 72□C 30 seconds. The PCR patterns were entered into SHGC RH server (www.shgc.stanford.edu) for analysis.

The results obtained with the G3 panel localized PAMP to chromosome 4p15-4p11 between markers D4S756 and D4S174.

Throughout this application various publications have been referenced within parentheses. The disclosures of these publications are hereby incorporated by reference in their entirety into this application in order to more fully describe the state of the art to which this invention pertains.

Although the invention has been described with reference to the disclosed embodiments, those skilled in the art will readily appreciate that the specific experiments detailed are only illustrative of the invention. It should be understood that various modifications can be made without departing from the spirit of the invention. Accordingly, the invention is limited only by the following claims.

---

What is claimed is:

1. A method to detect susceptibility to a prostate neoplastic condition in a subject, comprising:
   (a) measuring the expression level of PAMP RNA in said test sample obtained from said subject by selective hybridization with a PAMP nucleic acid probe of sufficient length to hybridize selectively to the coding region of SEQ ID NO:1 or its full complement, thereby determining the expression level of PAMP in said test sample; and
   (b) comparing said expression level of PAMP RNA in the test sample to the expression level of PAMP RNA in a standardized control sample,
   wherein said test sample is prostate tissue, blood, serum, urine or semen,
   wherein a test sample expression level of PAMP RNA of 2-fold or more greater than the expression level of PAMP RNA in said standardized control sample indicates susceptibility to a prostate neoplastic condition.

2. The method of claim 1, wherein said sample is prostate tissue.

3. The method of claim 1, wherein said expression level of PAMP RNA in the standardized control sample is determined using a normal prostate cell or an androgen-dependent cell line.

4. The method of claim 1, wherein said test sample is a fluid selected from the group consisting of blood, serum, urine and semen.

5. The method of claim 1, wherein said PAMP nucleic acid probe further comprises a detectable label.

6. A method to detect metastatic prostate cancer in a subject, comprising:
   (a) measuring the expression level of PAMP RNA in said test sample obtained from said subject by selective hybridization with a PAMP nucleic acid probe of sufficient length to hybridize selectively to the coding region of SEQ ID NO:1, or its full complement, thereby determining the expression level of PAMP in said test sample; and
   (b) comparing said expression level of PAMP RNA in the test sample to the expression level of PAMP RNA in a standardized control sample,
   wherein said test sample is prostate tissue, blood, serum, urine or semen,
   wherein a significant expression level of PAMP RNA in said test sample as compared to the expression level of PAMP RNA in said standardized control sample indicates the presence of metastatic prostate cancer.

7. The method of claim 6, wherein said sample is prostate tissue.

8. The method of claim 6, wherein said expression level of PAMP RNA in the standardized control sample is determined using a normal prostate cell or an androgen-dependent cell line.

9. The method of claim 6, wherein said test sample is a fluid selected from the group consisting of blood, serum, urine and semen.

10. The method of claim 6, wherein said PAMP nucleic acid probe further comprises a detectable label.

* * * * *